(12) United States Patent
Wall

(10) Patent No.: US 11,490,934 B1
(45) Date of Patent: Nov. 8, 2022

(54) SPINAL IMPLANT SYSTEM AND METHOD

(71) Applicant: WARSAW ORTHOPEDIC INC., Warsaw, IN (US)

(72) Inventor: Daniel Paxton Wall, Cordova, TX (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/527,467

(22) Filed: Nov. 16, 2021

(51) Int. Cl.
*A61B 17/88* (2006.01)
*A61B 17/70* (2006.01)

(52) U.S. Cl.
CPC .............................. *A61B 17/7082* (2013.01)

(58) Field of Classification Search
CPC ................................................ A61B 17/7082
USPC ......................................... 606/86 A, 99, 104
See application file for complete search history.

(56) References Cited

U.S. PATENT DOCUMENTS

| | | | |
|---|---|---|---|
| 10,448,978 B2 | 10/2019 | Wall et al. | |
| 2014/0148865 A1* | 5/2014 | Hennard | A61B 17/7086 606/86 A |
| 2014/0358186 A1* | 12/2014 | Frock | A61B 17/7062 606/86 A |
| 2015/0282855 A1* | 10/2015 | Bess | A61B 17/7082 606/86 A |
| 2018/0303522 A1 | 10/2018 | Wall et al. | |
| 2019/0029736 A1 | 1/2019 | Wall et al. | |
| 2020/0121397 A1* | 4/2020 | Elliott | A61B 34/20 |
| 2022/0125487 A1* | 4/2022 | Rezach | A61B 17/7091 |

* cited by examiner

*Primary Examiner* — Eduardo C Robert
*Assistant Examiner* — David C Comstock
(74) *Attorney, Agent, or Firm* — Sorell, Lenna & Schmidt, LLP

(57) ABSTRACT

An instrument includes an outer sleeve, an inner sleeve positioned in the outer sleeve, a latch coupled to the inner sleeve, a knob coupled to the inner sleeve and a lever coupled to the knob and to the latch. An inner sheath extends through an outer sheath and includes an end positioned between the inner sleeve and the shaft. The inner sheath includes a groove. The knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve. Systems, implants and methods are disclosed.

20 Claims, 25 Drawing Sheets

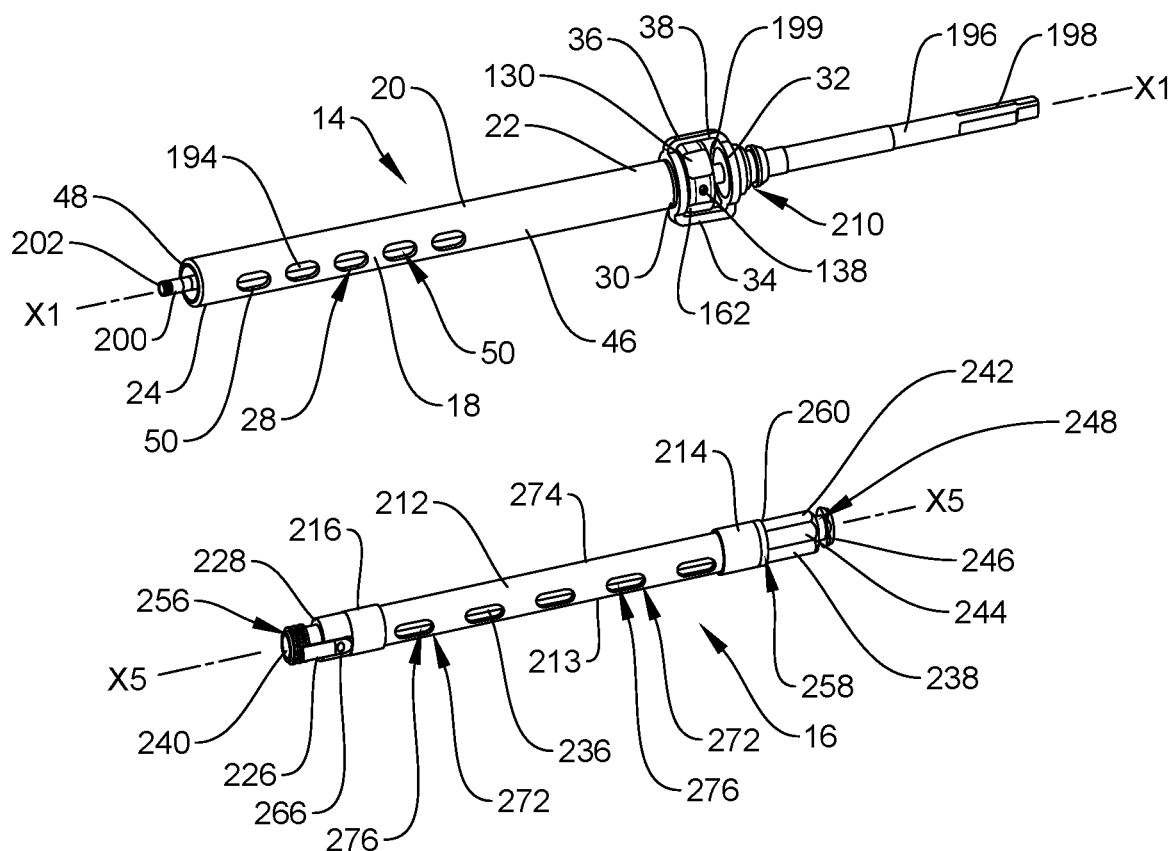
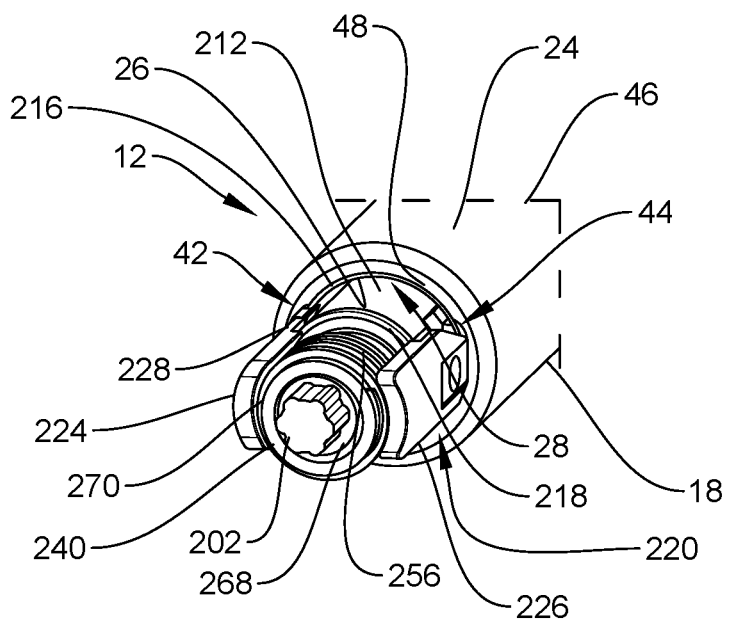
FIG. 3
FIG. 4

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises an outer assembly comprising an outer sleeve. An inner sleeve is positioned in the outer sleeve. A shaft extends through the sleeves. A latch is coupled to the inner sleeve. A knob is also coupled to the inner sleeve. A lever has a proximal end coupled to the knob and an opposite distal end coupled to the latch. A distal end of the shaft comprises a drive. An inner assembly comprises an outer sheath and an inner sheath extending through the outer sheath. The inner sheath has a proximal end positioned between the inner sleeve and the shaft and an opposite distal end comprising a threaded outer surface. The proximal end of the inner sheath includes a groove. The knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve. In some embodiments, systems, spinal implants and methods are disclosed.

In one embodiment, a surgical instrument includes an outer assembly comprising an outer sleeve defining a longitudinal axis. An inner sleeve is rotatably positioned in the outer sleeve. A shaft extends through the sleeves. A latch is coupled to the inner sleeve. A knob is also coupled to the inner sleeve. A lever has a proximal end coupled to the knob and an opposite distal end fixed to the latch. A distal end of the shaft comprises a drive configured for engagement with a socket of a shank of a bone screw. The shaft is permanently fixed relative to the outer sleeve. An inner assembly comprises an outer sheath and an inner sheath rotatably positioned in the outer sheath. The inner sheath has a proximal end positioned between the inner sleeve and the shaft and an opposite distal end comprising a threaded outer surface configured for engagement with a threaded inner surface of a head of the bone screw. The outer sheath comprises spaced apart tabs each configured for disposal between arms of the head. The proximal end of the inner sheath includes a circumferential groove. The knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve. The knob translates relative to the inner sleeve along the longitudinal axis to move the instrument between the first and second orientations. The latch pivots relative to the inner sleeve about a transverse axis that extends perpendicular to the longitudinal axis as the instrument moves between the first and second orientations. The inner sleeve has an inner surface defining a hexagonal configuration and the inner sheath comprises an outer surface having a hexagonal configuration that mates with the inner surface of the inner sleeve that defines the hexagonal configuration of the inner sleeve such that rotating the inner sleeve relative to the outer sleeve also rotates the inner sheath relative to the outer sleeve.

In one embodiment, a surgical system includes a bone screw comprising a shank and a receiver, such as, for example, a head rotatably coupled to the shank. The shank defines a socket. The head includes spaced apart arms defining an implant cavity therebetween. The arms each include a threaded inner surface. A surgical instrument comprises an outer assembly comprising an outer sleeve, an inner sleeve positioned in the outer sleeve, a shaft extending through the sleeves, a latch coupled to the inner sleeve, a knob coupled to the inner sleeve and a lever having a proximal end coupled to the knob and an opposite distal end coupled to the latch. A distal end of the shaft comprises a drive configured for disposal in the socket. An inner assembly comprises an outer sheath and an inner sheath extending through the outer sheath. The inner sheath has a proximal end positioned between the inner sleeve and the shaft and an opposite distal end comprising a threaded outer surface configured for engagement with the threaded inner surfaces of the arms. The outer sheath comprises spaced apart tabs each configured for disposal between the arms when the drive is positioned in the socket and the threaded outer surface engages the threaded inner surfaces. The proximal end of the inner sheath includes a groove. The knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve.

BRIEF DESCRIPTION OF THE DRAWINGS

The present disclosure will become more readily apparent from the specific description accompanied by the following drawings, in which:

FIG. 3 is a perspective view of components of the surgical instrument shown in FIG. 1;

FIG. 4 is a perspective view of components of the surgical instrument shown in FIG. 1;

DETAILED DESCRIPTION

Figure 1:
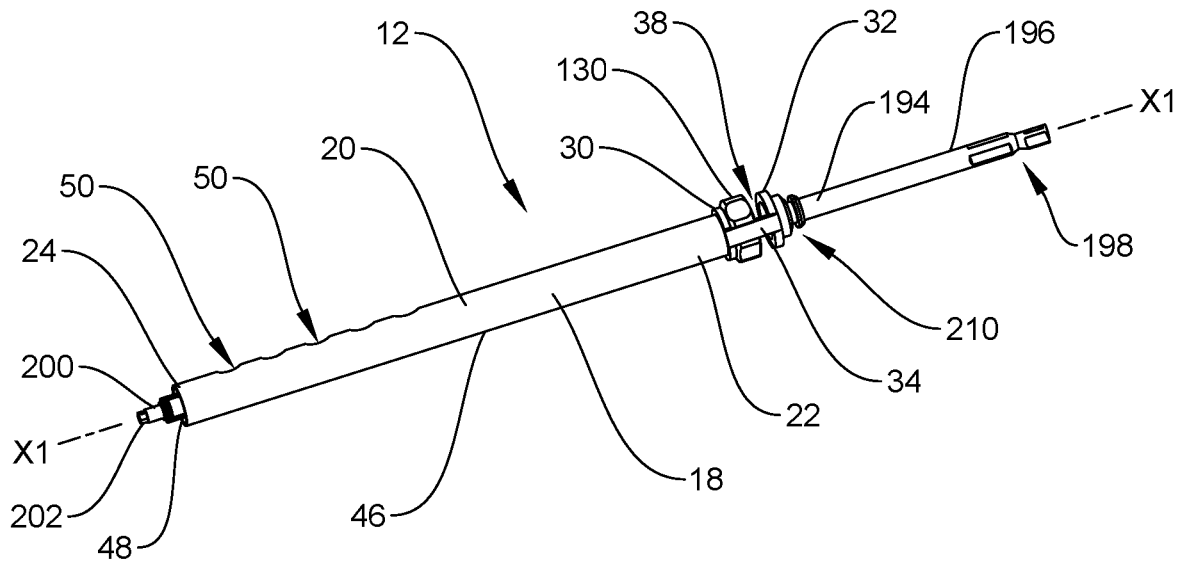
FIG. 1 is a perspective view of components of one embodiment of a surgical instrument of a surgical system, in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a screw driver that can be employed with bone fasteners to drive the bone fasteners into bone, for example. In some embodiments, the screw driver can easily connect and disconnect from a bone fastener. In some embodiments, the screw driver can be employed with an end effector of a robotic arm to facilitate movement of the screw driver via the robotic arm. In some embodiments, the screw driver is guided through the end effector for a guide-wireless screw insertion. In some embodiments, the screw driver comprises a robot screw driver employed with robotic and/or navigation guidance, which may include an image guide.

In some embodiments, the present surgical system includes a screw driver configured for use with a robot, such as, for example, a Mazor robot to deliver screws during a surgical procedure, such as, for example, minimally invasive transforaminal lumbar interbody fusion (TLIF). The screw driver includes an inner assembly having inner and outer sheaths that are connected to the screw such that instruments, for example, can be delivered through the inner assembly to the head of the screw. In particular, the screw driver includes a disengagement feature in a knob of the screw driver that allows the inner assembly of the screw driver to be left on the head of the screw when an outer assembly of the screw driver is removed from the screw and the inner assembly. This allows a surgeon to disengage and/or remove the outer assembly yet still guide other instruments down to the head of the screw via the inner assembly.

In some embodiments, the screw driver is configured for use with different types of bone fasteners or screws, such as, for example, screws having different sizes and/or structural configurations. In some embodiments, the head of the screw includes a tulip slot and the part of the screw driver that engages the tulip slot is on the inner assembly. In particular, in some embodiments, the outer sheath of the inner assembly includes a pair of tabs that are configured for positioning in the tulip slots of a head of a screw and the inner sheath has a threaded outer surface that engages threaded inner surfaces of arms of the head, while the tabs are positioned in the tulip slots. This allows the inner assembly to hold the head of the screw in a selected position relative to the shank of the screw while a drive of the outer assembly is positioned in a socket of the shank and rotates the shank of the screw, as discussed herein.

In some embodiments, the screw driver is assembled by inserting the inner assembly into the outer assembly. In some embodiments, a hex of the inner sheath of the inner assembly is aligned with a hex of a knob sleeve or inner sleeve of the outer assembly by pushing the inner assembly from the distal end and pushing on the knob from the proximal end. Tabs on the outer sheath of the inner assembly are aligned with recesses in the outer assembly as the inner assembly translates within the outer assembly. In some embodiments, the inner assembly is configured to snap into the outer assembly. In some embodiments, inserting the inner assembly into the outer assembly causes spring loaded latches of the outer assembly to snap back on insertion of the inner assembly and retain it once loaded. In some embodiments, the spring loaded latches include tabs that are inserted into a groove of the inner assembly when the inner assembly is inserted into the outer assembly in a manner that prevents the inner assembly from translating relative to the outer assembly, as discussed herein.

To remove the outer assembly from the inner assembly and the screw after driving the shank of the screw into tissue, such as, for example, bone, the surgeon pulls up on the knob (proximal direction) while pulling back on the outer assembly. Release latches are keyed to the knob by pins such that the levers spring open when the knob is pulled proximally. The outer assembly can then be removed from the inner assembly and the screw while leaving the inner assembly threaded into the head of the screw. In some embodiments, pulling up on the knob while pulling back on the outer assembly disengages the spring loaded latches from the inner assembly such that the tabs of the spring loaded latches exit the groove of the inner assembly to allow the outer assembly to translate proximally and/or distally relative to the inner assembly.

In some embodiments, the same inner assembly can be used with different size outer assemblies. For example, the outer assembly can have different lengths to accommodate scenarios in which short and long drivers are needed. Allowing the same inner assembly to be used with different size (length) outer assemblies reduces the number of instruments and/or components used in connection with a selected surgical procedure. This also allows the inner assembly to remain rather short relative to the outer assembly, which prevents the inner assembly from interfering with a robot arm. That is, the relatively short length of the inner assembly allows a robot arm to move without hitting into the inner assembly as the robot arm moves the screw driver relative to the patient. The configuration of the inner assembly allows the inner assembly to engage the tulip head of the screw so that the screw can be manipulated from the proximal end, as discussed herein.

As briefly discussed above, the inner assembly includes a two sheath assembly having the outer sheath and the inner sheath rotatably disposed within the outer sheath. The inner sheath and the outer sheath are held together by two pins that are pressed in and welded such that the inner sheath can spin within the outer sheath. In some embodiments, the inner sheath and/or the outer sheath include one or a plurality of clean out slots. In some embodiments, the outer sheath includes a notch that is aligned within one of the tabs of the outer sheath that engage the tulip head to allow the notch to be used as a visual indicator of how the rod slot of the screw is aligned and/or aid in positioning of the screw.

In some embodiments, the outer sleeve assembly includes a drive shaft that is one piece with an outer sleeve of the outer assembly. In some embodiments, the drive shaft is welded to the outer sleeve. A distal end of the drive shaft includes a drive, such as, for example, a drive tip configured for disposal in the socket of the shank of the screw such that rotation of the shaft of the outer assembly also rotates the shank of the screw to drive the shank into tissue, such as, for example, bone. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the inner sheath includes a male thread configured to mate with one or more female threads of a receiver of a bone fastener to resist and/or prevent disengagement of the inner sheath from the receiver.

In some embodiments, the knob and the knob sleeve are keyed together and turn together. In some embodiments, the knob is spring biased by four springs (about 5 lbsf axial). In some embodiments, pins key and retain the knob after assembly.

In some embodiments, the screw driver is configured for use with robotic surgery. In some embodiments, the screw driver can be employed with fixed-axis screws (FAS), uni-axial screws (UAS), sagittal adjusting screws (SAS), transverse sagittal adjusting screws (TSAS) and multi-axial screws (MAS) screws, and allows the screws to be driven through a robotic end effector.

In some embodiments, a method of assembling components of the present system includes the step of connecting a bone screw to the screw driver. In some embodiments, the method includes the step of inserting the drive tip of a shaft of the outer assembly into a drive socket of the bone screw. In some embodiments, the method includes the step of rotating the knob of the screw driver to tighten and pull the bone screw tight against the screw driver.

In some embodiments, the surgical system is employed with a method for treating spinal trauma and/or deformity disorders. In some embodiments, the surgical system is employed with a method for treating spinal trauma and/or deformity disorders with a minimally invasive surgical technique.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-40, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. In some embodiments, driver 12 is configured to be employed with an end effector of a robotic arm wherein driver 12 is guided through the end effector for guide-wireless insertion of a spinal implant, such as, for example, a bone fastener, as discussed in U.S. patent application Ser. No. 15/492,867, U.S. patent application Ser. No. 15/661,962 and/or U.S. patent application Ser. No. 15/661,986, the contents of which are incorporated herein by reference, in their entireties.

Driver 12 includes an outer assembly 14 and an inner assembly 16 configured for removable engagement with assembly 14. Assembly 14 includes an outer sleeve 18. Sleeve 18 includes a body 20 extending along a central longitudinal axis X1 between a proximal end 22 and an opposite distal end 24. Body 20 includes an inner surface 26 defining a passageway 28. Sleeve 18 includes a plate 30 coupled to end 22 and a plate 32 that is connected to plate 30 by bifurcated arms 34, 36. Plates 30, 32 and arms 34, 36 define an aperture 38. Aperture 38 is in communication with passageway 28 via an opening 40 that extends through plate 30. In some embodiments, passageway 28, aperture 38 and/or opening 40 extend parallel to axis X1. In some embodiments, passageway 28, aperture 38 and/or opening 40 are coaxial with axis X1. In some embodiments, passageway 28, aperture 38 and/or opening 40 may be disposed at alternate orientations, relative to X1, such as, for example, transverse, perpendicular and/or other angular orientations such as acute or obtuse, co-axial and/or may be offset or staggered. In some embodiments, passageway 28, aperture 38 and/or opening may have various cross section configurations, such as, for example, circular, oval, oblong, triangular, rectangular, square, polygonal, irregular, uniform, non-uniform, variable, tubular and/or tapered. In some embodiments, sleeve 18 is monolithic. In some embodiments, plates 30, 32 and arms 34, 36 are integrally and/or monolithically formed with body 20.

Figure 11:
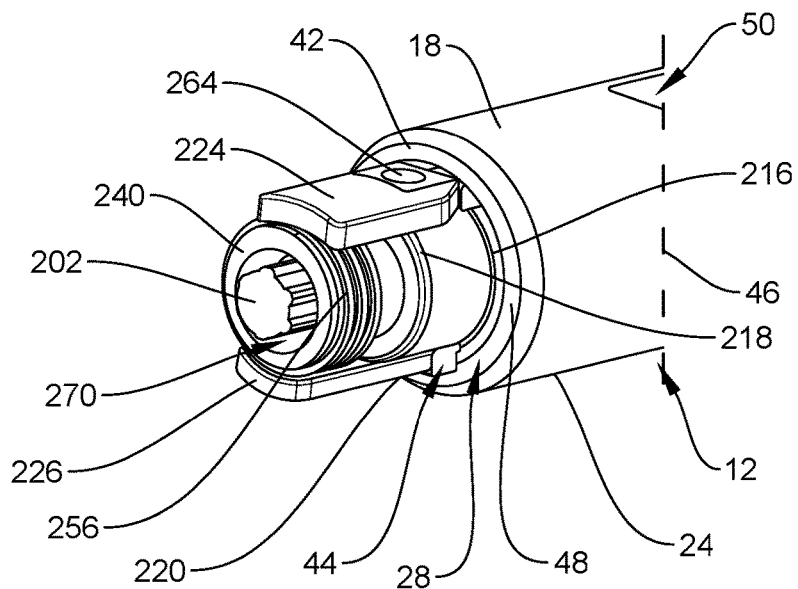
FIG. 11 is a perspective view of components of the surgical instrument shown in FIG. 1.

In some embodiments, end 24 is cylindrical or substantially cylindrical and includes spaced apart slots, such as, for example, recesses 42, 44 extending into surface 26, as best shown in FIGS. 4 and 11, for example. In particular, recesses 42, 44 each extend into surface 26 without extending through an opposite outer surface 46 of body 20 and are configured for disposal of tabs 224, 226 of assembly 16 to align assembly 16 with assembly 14 as assembly 16 is being connected with assembly 14, as discussed herein. In some embodiments, recesses 42, 44 each extend through a distal end surface 48 of end 24 wherein end surface 48 extends perpendicular to axis X1. In some embodiments, recess 42 and/or recess 44 extend parallel to axis X1. In some embodiments, recess 42 and/or recess 44 may have various cross section configurations, such as, for example, circular, oval, oblong, triangular, rectangular, square, polygonal, irregular, uniform, non-uniform, variable, tubular and/or tapered.

Figure 2:
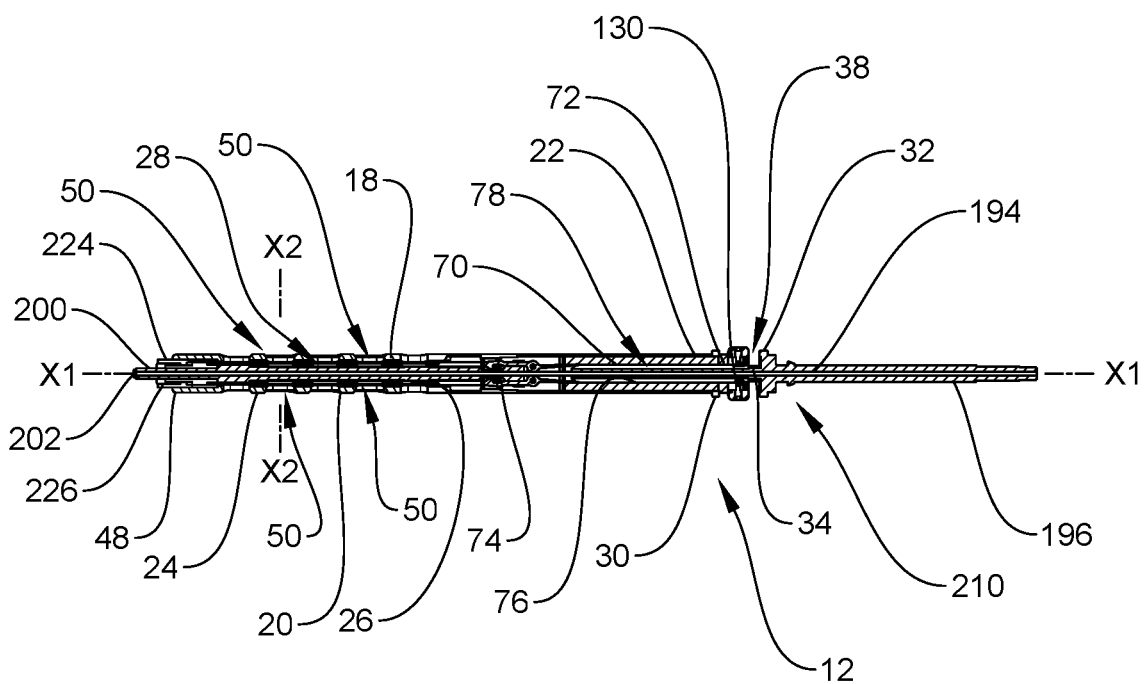
FIG. 2 is a side, cross-sectional view of the surgical instrument shown in FIG. 1.
Figure 5:
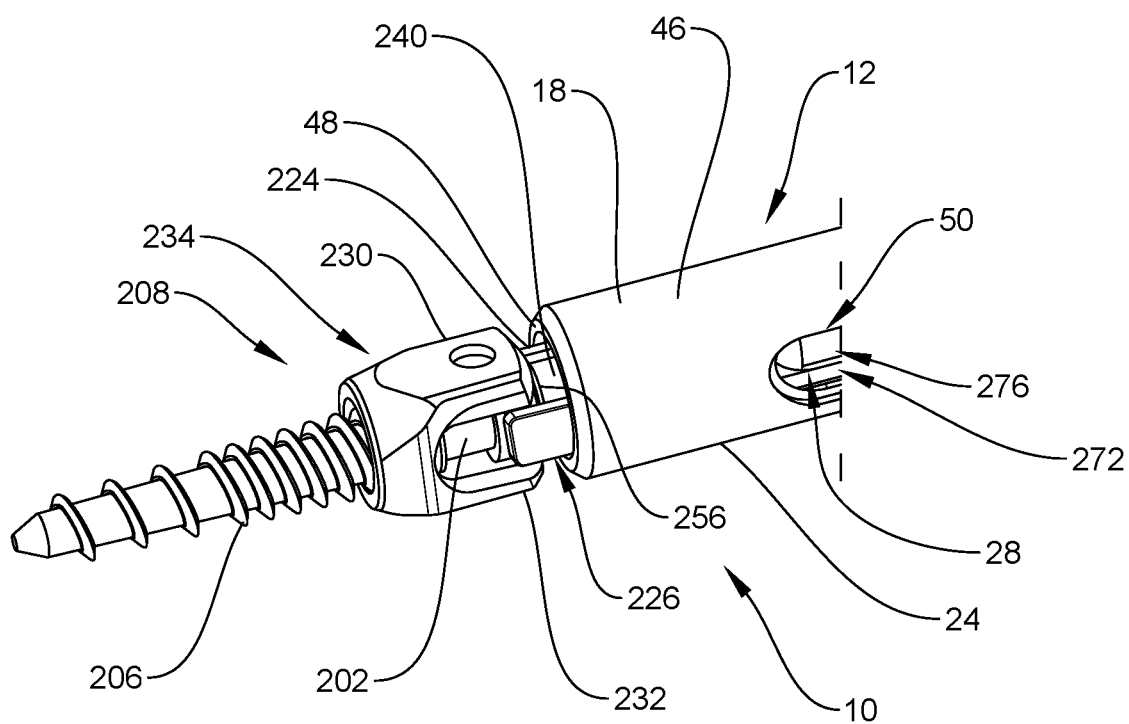
FIG. 5 is a perspective view of an implant of the system and a portion of the surgical instrument shown in FIG. 1.
Figure 6:
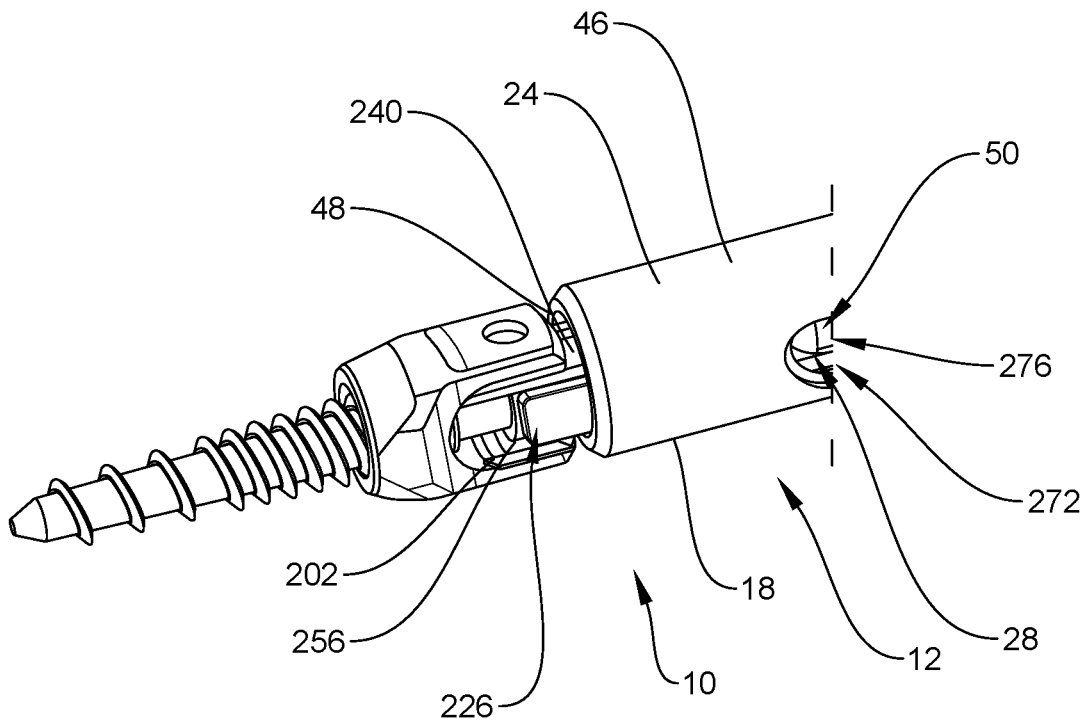
FIG. 6 is a perspective view of an implant of the system and a portion of the surgical instrument shown in FIG. 1.
Figure 15:
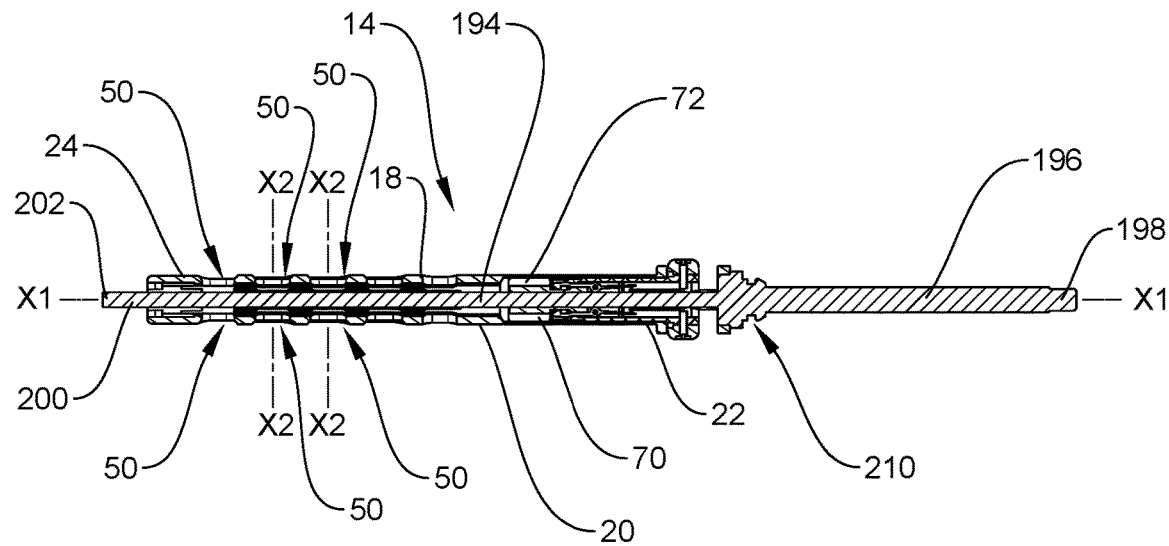
FIG. 15 is a side, cross-sectional view of components of the surgical instrument shown in FIG. 1.
Figure 16:
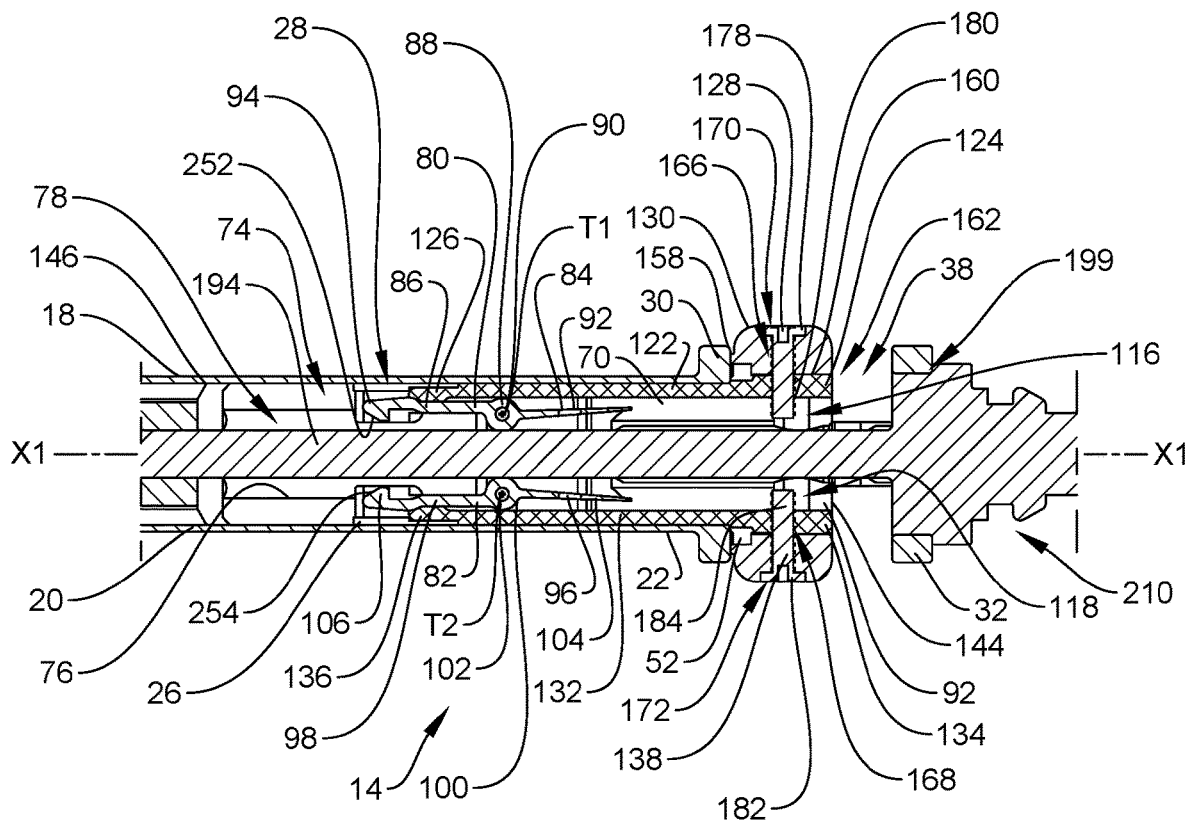
FIG. 16 is a side, cross-sectional view of components of the surgical instrument shown in FIG. 1.
Figure 17:
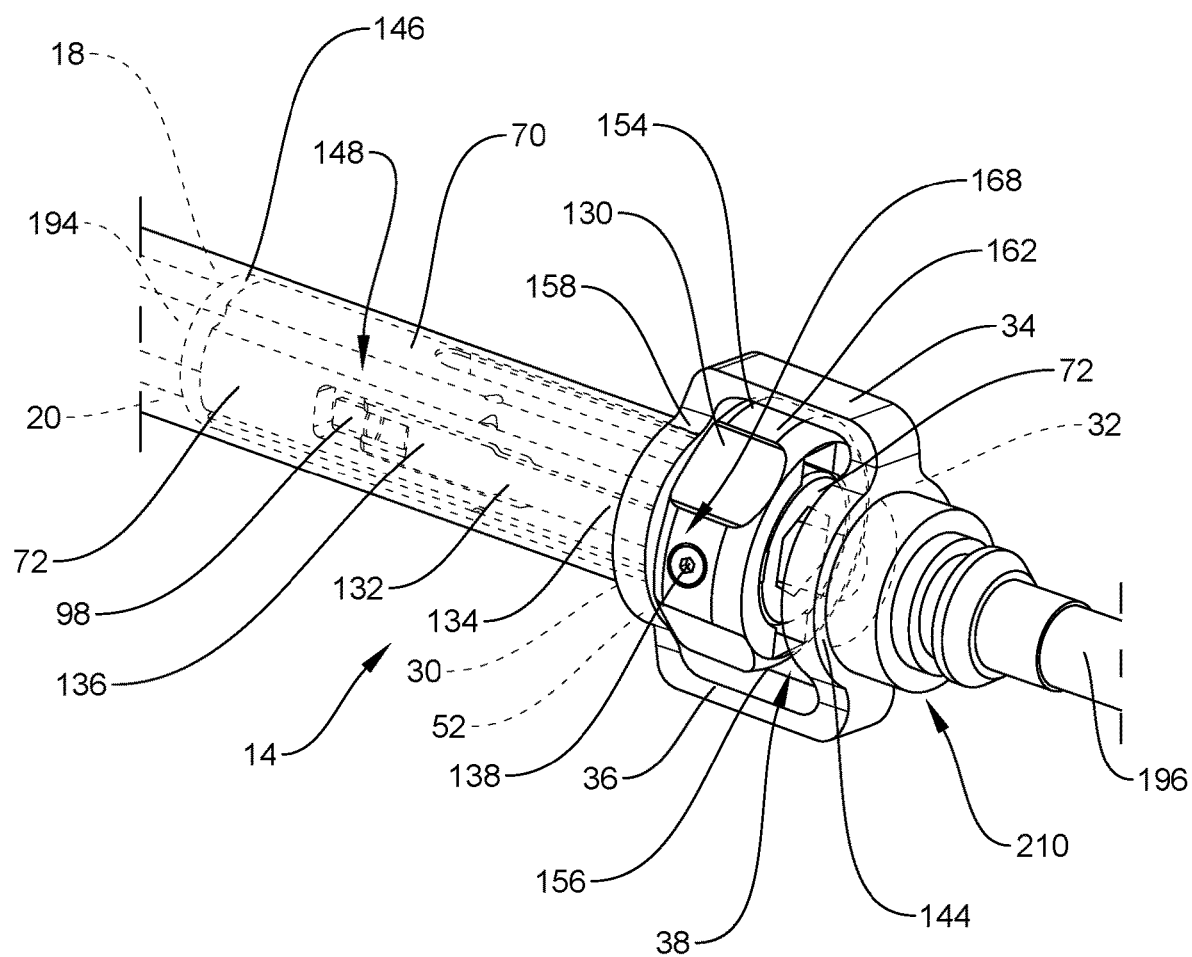
FIG. 17 is a perspective view, in part phantom, of components of the surgical instrument shown in FIG. 1.
Figure 18:
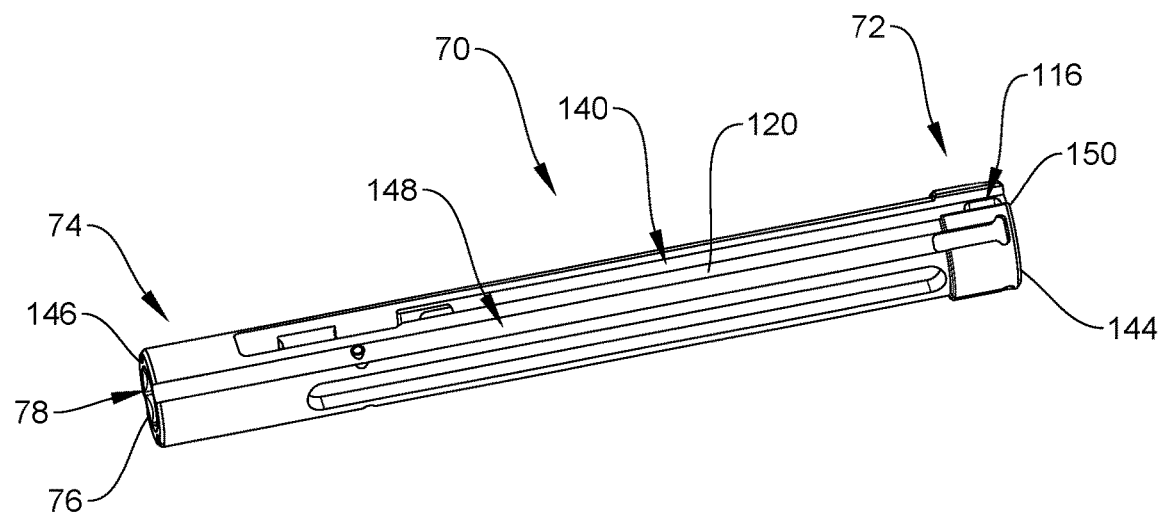
FIG. 18 is a perspective view of a component of the surgical instrument shown in FIG. 1.
Figure 19:
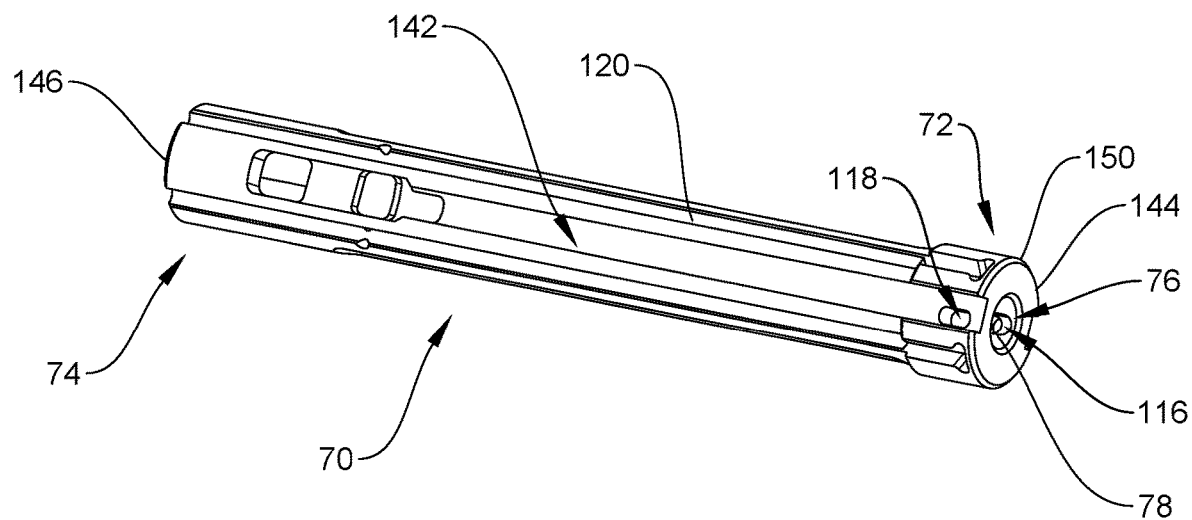
FIG. 19 is a perspective view of the component shown in FIG. 18.
Figure 20:
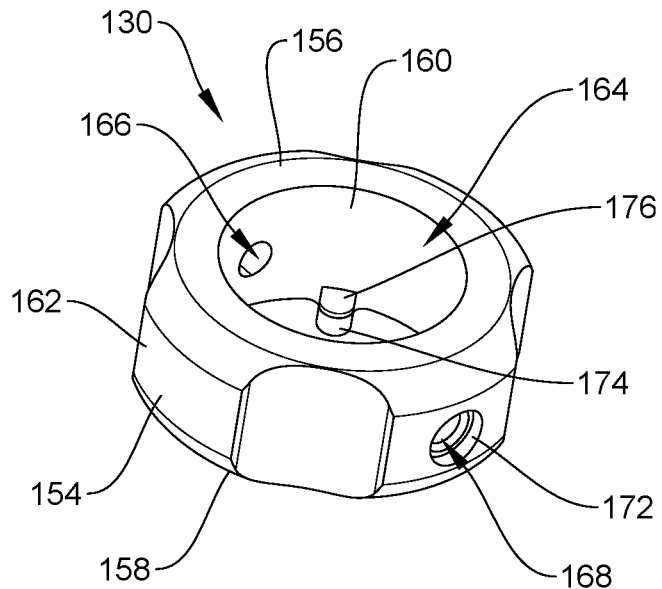
FIG. 20 is a perspective view of a component of the surgical instrument shown in FIG. 1.
Figure 21:
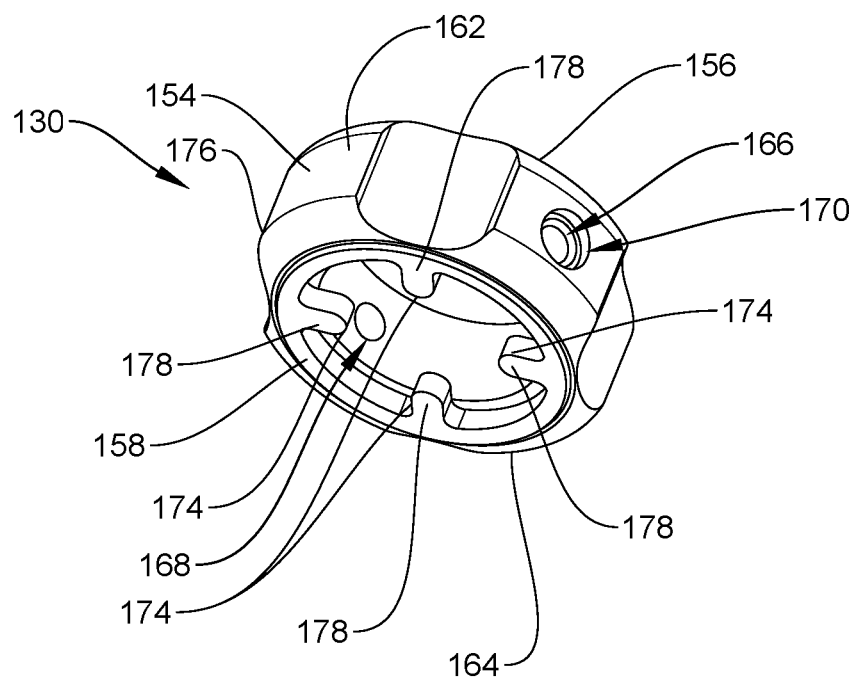
FIG. 21 is a perspective view of the component shown in FIG. 20.
Figure 22:
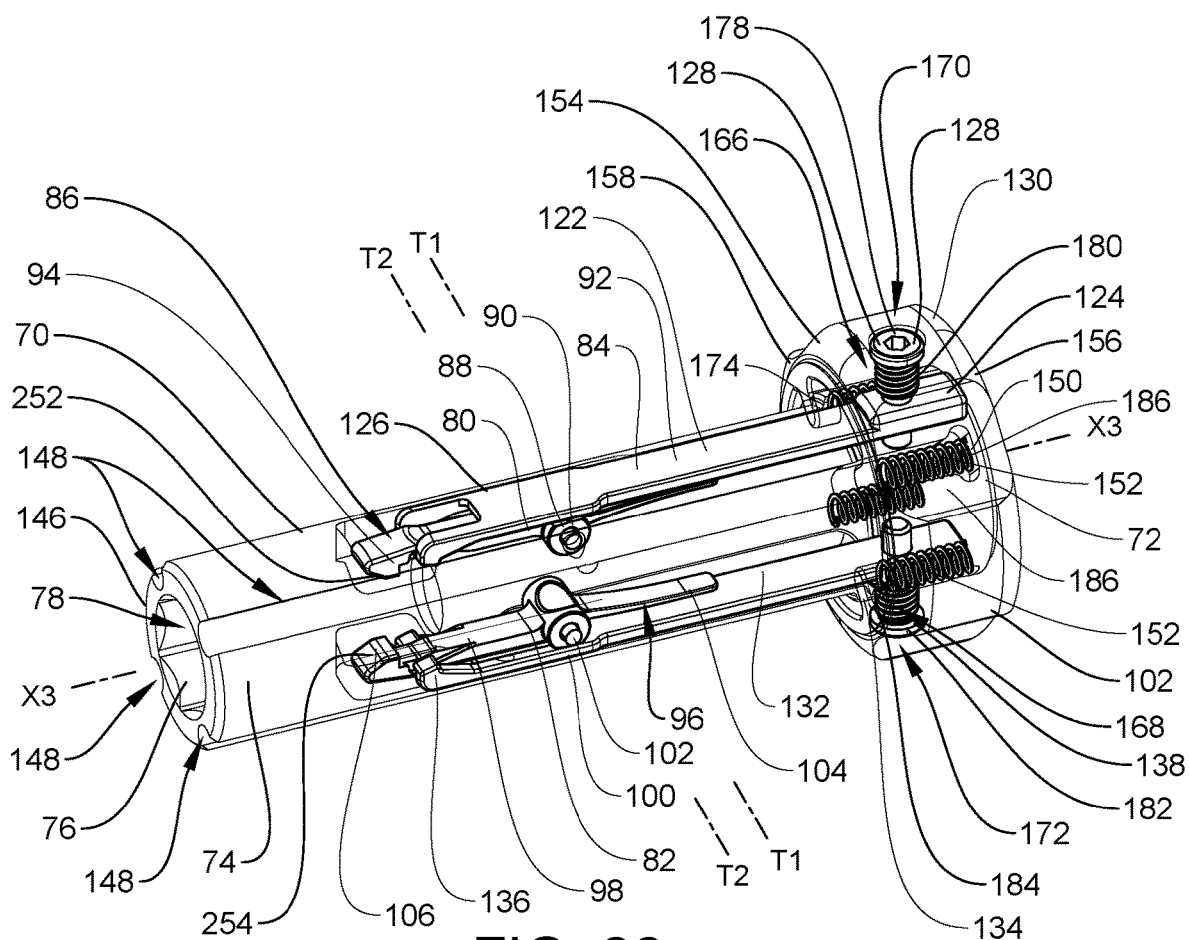
FIG. 22 is a perspective view, in part phantom, of components of the surgical instrument shown in FIG. 1.
Figure 23:
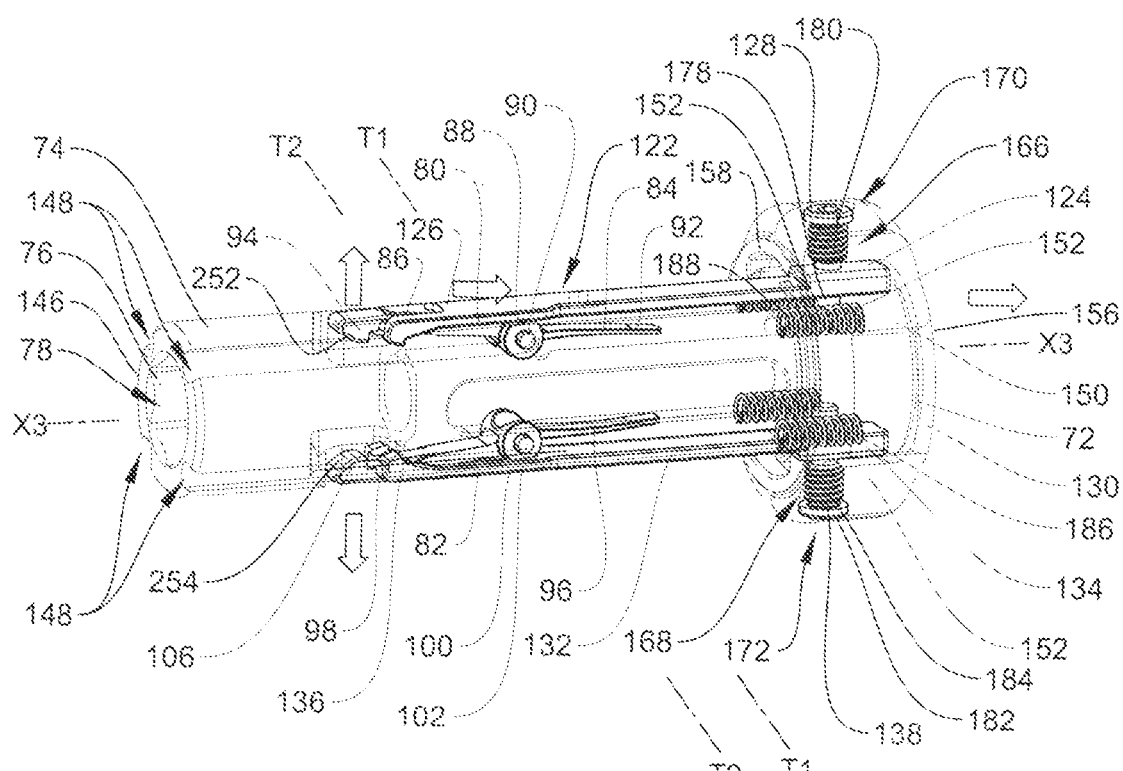
FIG. 23 is a perspective view, in part phantom, of components of the surgical instrument shown in FIG. 1.
Figure 24:
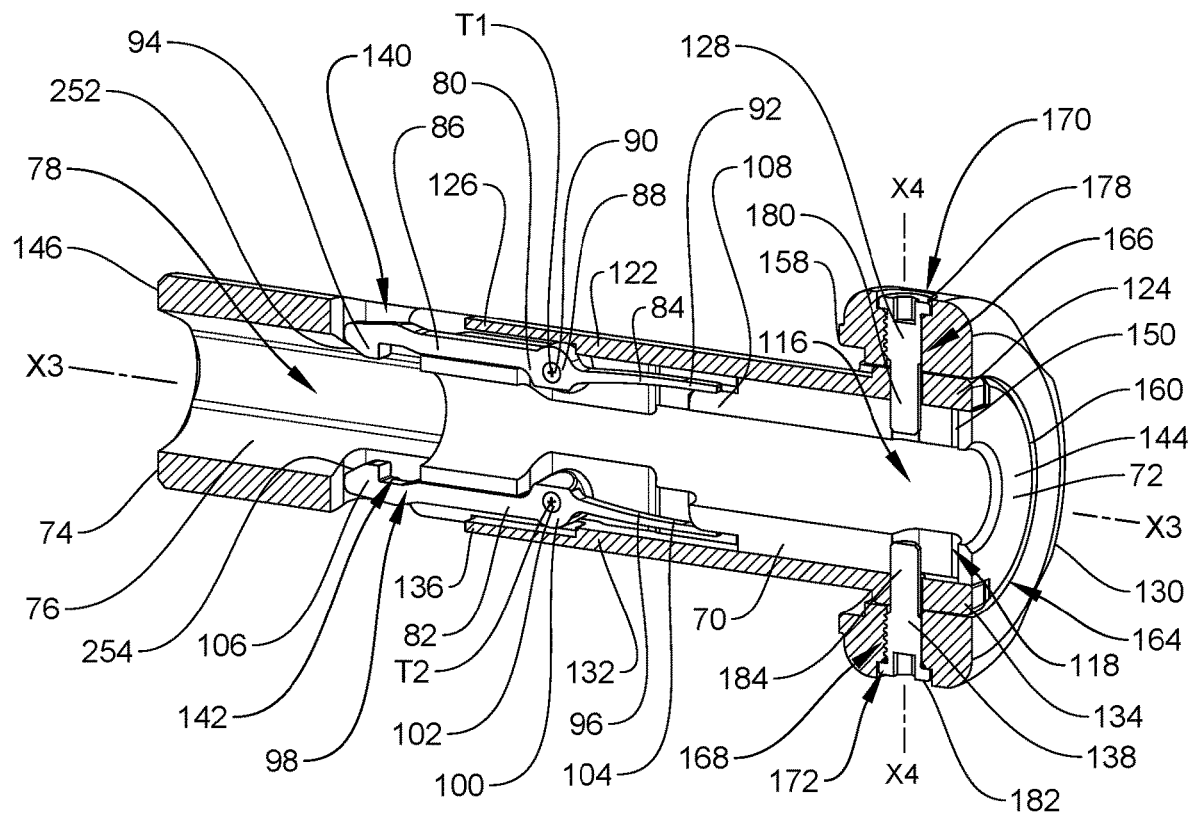
FIG. 24 is a perspective, cross-sectional view of components of the surgical instrument shown in FIG. 1.
Figure 25:
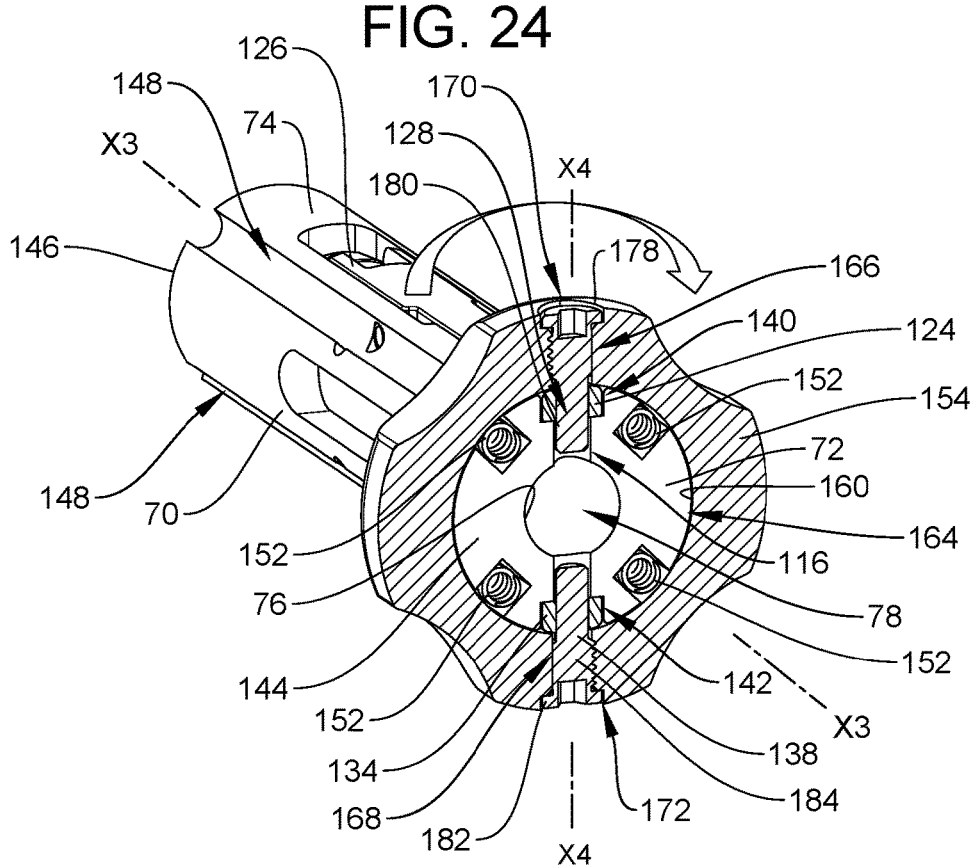
FIG. 25 is a perspective, cross-sectional view of components of the surgical instrument shown in FIG. 1.
Figure 26:
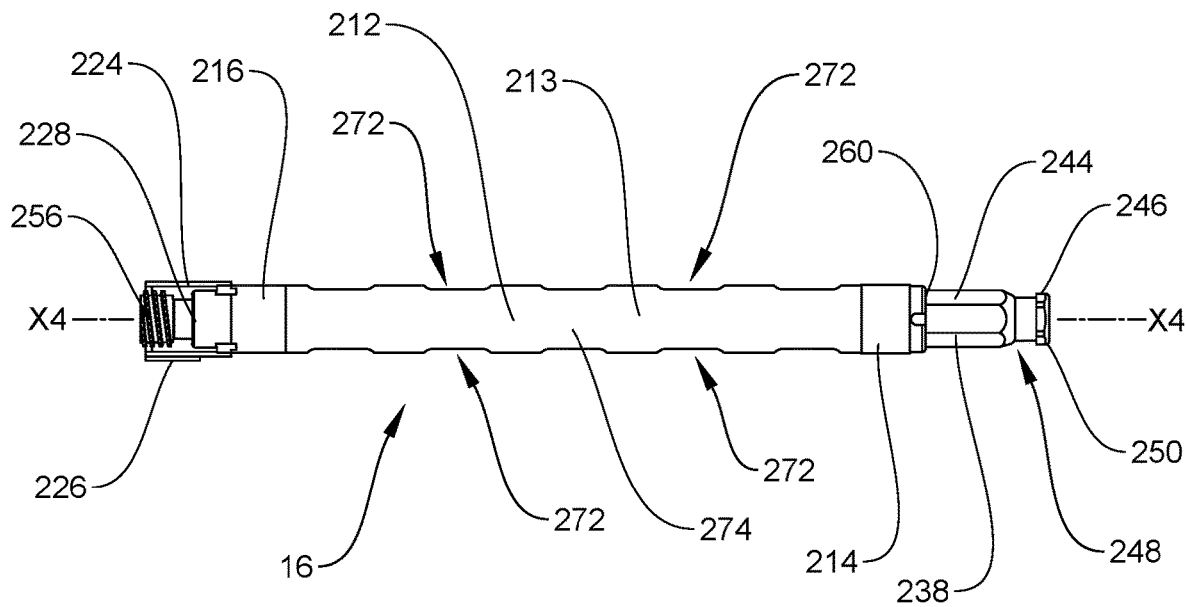
FIG. 26 is a side view of components of the surgical instrument shown in FIG. 1.
Figure 27:
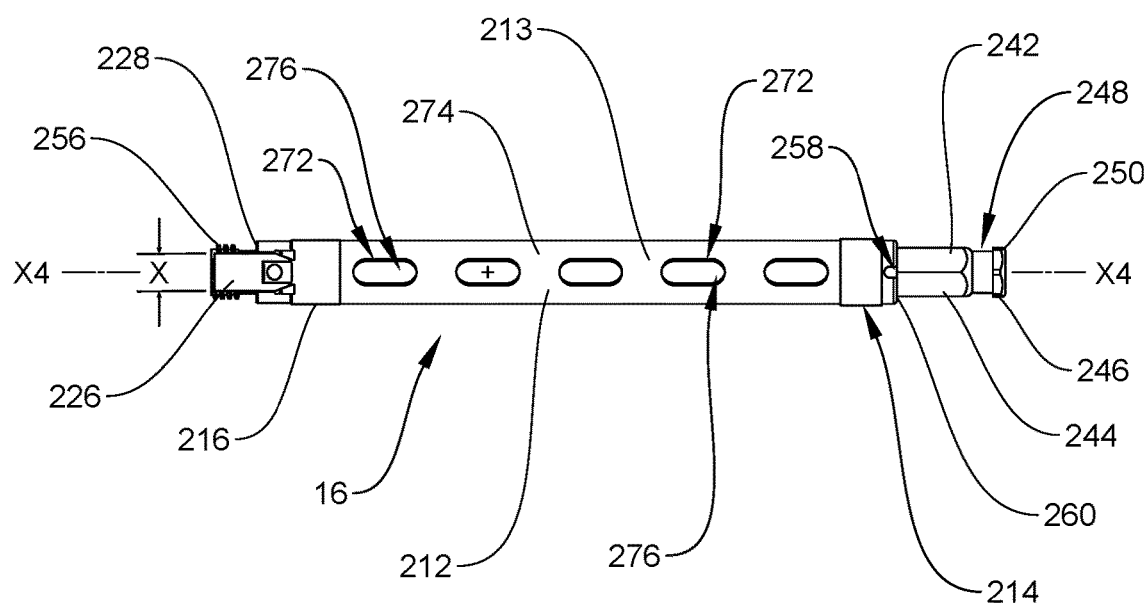
FIG. 27 is a side view of components of the surgical instrument shown in FIG. 1.
Figure 28:
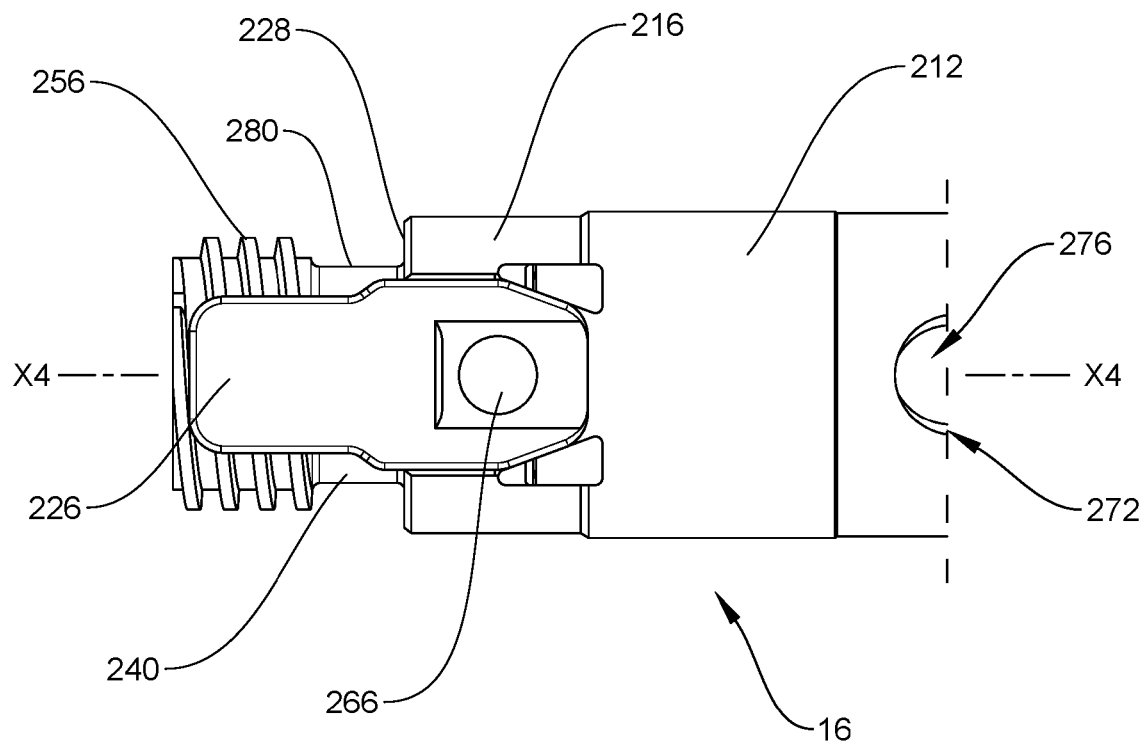
FIG. 28 is a close-up, side view of components of the surgical instrument shown in FIG. 1.

In some embodiments, sleeve 18 includes one or a plurality of slots 50 in body 20 that each extend through surface 26 and surface 46. In embodiments wherein body 20 includes a plurality of slots 50, slots 50 are spaced apart from one another. In some embodiments wherein body 20 includes a plurality of slots 50, slots 50 extend parallel to axis X1 and are disposed in a serial configuration along axis X1. For example, in some embodiments, slots 50 are arranged in one or more columns that each extend parallel to axis X1. In some embodiments, body 20 includes three or more columns of slots 50, wherein the columns are uniformly spaced apart about axis X1. In some embodiments, body 20 includes two opposing columns of slots 50 such that each of the slots 50 in one column is aligned with one of the slots 50 in the other column along an axis X2 that extends perpendicular to axis X1, as can be seen in FIGS. 2 and 15, for example. It is envisioned that slots 50 may be useful for cleaning driver 12 and/or visualizing components of driver 12 or another instrument within passageway 28. In some embodiments, slots 50 may be variously shaped, such as, for example, circular, oval, oblong, triangular, square, polygonal, irregular, uniform, non-uniform, offset, staggered, undulating, arcuate, variable and/or tapered.

Assembly 14 includes a knob sleeve, such as, for example an inner sleeve 70 extending through opening 40. Sleeve 70 extends along a central longitudinal axis X3 between a proximal portion 72 that is rotatably positioned in aperture 38 and an opposite distal portion 74 rotatably positioned in passageway 28. An inner surface 76 of sleeve 70 defines a bore 78 configured for disposal of assembly 16, as discussed herein. In some embodiments, surface 76 is shaped and/or configured to provide at least a portion of bore 78 with a hexagonal configuration for disposal of a portion of assembly 16 having a hexagonal configuration such that rotating sleeve 70 relative to sleeve 18 also rotates assembly 16 relative to sleeve 18, as discussed herein. In some embodiments, bore 78 and/or the portion of assembly 16 configured for disposal in bore 78 may have various cross section configurations, such as, for example, circular, oval, oblong, triangular, rectangular, square, polygonal, irregular, uniform, non-uniform, variable, tubular and/or tapered.

Driver 12 includes spaced apart latches 80, 82 coupled to sleeve 70 such that latches 80, 82 are rotatable relative to sleeve 70. In particular, latch 80 includes an end 84, and end 86 and a hub 88 positioned between ends 84, 86. A pin 90 extends through hub 88 and sleeve 70 along a transverse axis T1 such that latch 80 is rotatable relative to sleeve 70 about pin 90 and/or axis T1. End 84 includes a leaf spring 92 and end 86 includes a tab 94 configured for engagement with a groove of assembly 16 to move driver 12 between a first orientation in which tab 94 is disposed in the groove of assembly 16 and assembly 16 is prevented from translating relative to assembly 18 along axis X1 and a second orientation in which tab 94 is spaced apart from the groove of assembly 16 and assembly 16 is capable of translating relative to assembly 18 along axis X1. Likewise, latch 82 includes an end 96, and end 98 and a hub 100 positioned between ends 96, 98. A pin 102 extends through hub 100 and sleeve 70 along a transverse axis T2 such that latch 82 is rotatable relative to sleeve 70 about pin 102 and/or axis T2. End 96 includes a leaf spring 104 and end 98 includes a tab 106 configured for engagement with the groove of assembly 16 to move driver 12 between the first orientation in which tab 106 is disposed in the groove of assembly 16 and assembly 16 is prevented from translating relative to assembly 18 along axis X1 and the second orientation in which tab 106 is spaced apart from the groove of assembly 16 and assembly 16 is capable of translating relative to assembly 18 along axis X1. Latches 80, 82 are configured to pivot relative to sleeve 70 about pins 90, 102 to allow tabs 94, 106 to move in and out of the groove in assembly 16 as driver 12 moves between the first and second orientations, as discussed herein. In some embodiments, axes T1, T2 extend parallel to one another. In some embodiments, axes T1, T2 extend perpendicular to axis X3. In some embodiments, axis T1 and/or axis T2 may be disposed at alternate orientations, relative to axis X3, such as, for example, transverse, perpendicular and/or other angular orientations such as acute or obtuse, co-axial and/or may be offset or staggered.

Portion 72 includes opposite first and second slots 116, 118 each extending though surface 76 and an opposite outer surface 120 of sleeve 70 such that slot 116 is spaced apart from slot 118 and slot 116 is aligned with slot 118 along a transverse axis X4 that extends perpendicular to axis X3. A lever 122 includes an end 124 and an opposite end 126 that is coupled to end 86 of latch 80. A pin 128 extends through a knob 130 and end 124 of lever 122 and into slot 116 to couple lever 122 to latch 80 and knob 130. A lever 132 is positioned opposite lever 122 and includes an end 134 and an opposite end 136 that is coupled to end 98 of latch 82. A pin 138 extends through knob 130 and end 134 of lever 132 and into slot 118 to couple lever 132 to latch 82 and knob 130. In some embodiments, end 126 is fixed to end 86 and/or end 136 is fixed to end 98. In some embodiments, end 126 is permanently fixed to end 86 and/or end 136 is permanently fixed to end 98. In some embodiments, end 126 is integrally and/or monolithically formed with end 86 and/or end 136 is integrally and/or monolithically formed with end 98. Slot 116 has a length that is greater than a diameter of pin 128 such that pin 128 is able to translate relative to sleeve 70 along axis X3 within slot 116 and slot 118 has a length that is greater than a diameter of pin 138 such that pin 138 is able to translate relative to sleeve 70 along axis X3 within slot 118. In some embodiments, knob 130 translates proximally relative to sleeve 70 to move pins 128, 138 within slots 116, 118 to move driver from the first orientation to the second orientation, as discussed herein. In some embodiments, end 126 can be variously connected with end 86 and/or end 136 can be variously connected with end 98, such as, for example, monolithic, integral connection, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

In some embodiments, lever 122 is movably disposed in a slot 140 of sleeve 70 as driver 12 moves between the first and second orientations and lever 132 is movably disposed in a slot 142 of sleeve 70 as driver 12 moves between the first and second orientations. In some embodiments, slots 140, 142 each extend through surfaces 76, 120 and a proximal end surface 144 without extending through an opposite distal end surface 146 of sleeve 70 to prevent levers 122, 132 from translating relative to sleeve 70 distal to slots 140, 142.

Sleeve 70 defines a plurality of spaced apart grooves 148 extending into surface 120 without extending through surface 76. In some embodiments, sleeve 70 includes four grooves 148, which are equally spaced apart from one another about sleeve 70 and/or axis X3. That is, grooves 148 are spaced radially about sleeve 70 and/or axis X3 such that grooves 148 are each spaced ninety degrees from an adjacent one of grooves 148. Grooves 148 are configured for disposal of springs 152 to bias knob 130 in a distal direction relative to sleeve 70, which biases driver 12 to the first orientation, as discussed herein. In some embodiments, grooves 148 each extend parallel to axis X3. Grooves 148 each extend through end surface 146 without extending through end surface 144 such that ends of springs 152 directly engage a wall 150 that defines surface 144 when springs 152 are positioned in grooves 148, as discussed herein.

Knob 130 coupled to sleeve 70 such that knob 130 is rotatably positioned in aperture 38. Knob 130 includes a wall 154 including a proximal surface 156 and an opposite distal surface 158. Wall 154 includes an inner surface 160 and an opposite outer surface 162. Surfaces 160, 162 extend from surface 156 to surface 158. Surface 160 defines a channel 164 extending through surface 156 and surface 158. Portion 72 of sleeve 70 is positioned in channel 164. Knob 130 includes a first pin hole 166 and a second pin hole 168 that is spaced apart from hole 166 such that hole 168 is aligned with hole 166. Holes 166, 168 each extend through surfaces 160, 162 such that holes 166, 168 are each in communication with channel 164. Hole 166 is aligned with slot 116 when knob 130 is coupled to sleeve 70 such that pin 128 extends through hole 166 and into slot 116 and hole 168 is aligned with slot 118 when knob 130 is coupled to sleeve 70 such that pin 138 extends through hole 168 and into slot 118. The arrangement of pins 128, 138 with knob 130 and sleeve 70 keys knob 130 and sleeve 70 together such that rotation of knob 130 relative to sleeve 18 about axis X1 also rotates sleeve 70 relative to sleeve 18 about axis X1 and/or rotation of sleeve 70 relative to sleeve 18 about axis X1 also rotates knob 130 relative to sleeve 18 about axis X1. Due to the alignment of slots 116, 118 and the alignment of holes 166, 168, pin 128 is coaxial with pin 138 along axis X4. In some embodiments, hole 166 defines a female thread form configured for engagement with a male thread form of pin 128 and hole 168 defines a female thread form configured for engagement with a male thread form of pin 138.

In some embodiments, knob 130 includes a first counterbore 170 in communication with hole 166 and a second counterbore 172 in communication with hole 168. This allows a head 178 of pin 128 to be disposed entirely within counterbore 170 while a shaft 180 of pin 128 is disposed in hole 166 and a head 182 of pin 138 to be disposed entirely within counterbore 172 while a shaft 184 of pin 138 is disposed in hole 168. Disposing heads 178, 182 entirely within counterbores 170, 172 prevents pins 128, 138 from extending outwardly from surface 162 to facilitate gripping of knob 130 by hand.

Knob 130 includes a plurality of spaced apart tabs 174 extending outwardly from surface 160 such that tabs 174 are disposed radially about knob 130. In some embodiments, knob 130 includes four tabs 174, wherein each tab 174 is aligned with one of grooves 148 when knob 130 is coupled to sleeve 70. Tabs 174 each include a proximal surface 176 and an opposite distal surface 178 that is flush with surface 158. The alignment of tabs 174 with grooves 148 allows proximal ends 186 of springs 152 to directly engage wall 150 and opposite distal ends 188 of springs 152 to directly engage one of surfaces 186 when springs 152 are disposed in grooves 148. The arrangement of springs 152 with knob 130 and sleeve 70 biases knob 130 relative to sleeve 70 such that surface 158 of knob 130 directly engages a proximal surface 52 of plate 30, as discussed herein. That is, a force is required to overcome the force provided by springs 152 to allow knob 130 to be moved proximally along axis X1 relative to sleeve 18 such that surface 158 of knob 130 is spaced apart from surface 52 of plate 30. In some embodiments, surface 158 of knob 130 directly engages surface 52 of plate 30 such that springs 152 bias driver 12 to the first orientation and a force is required to overcome the force provided by springs 152 to allow knob 130 to be moved proximally along axis X1 relative to sleeve 18 such that surface 158 of knob 130 is spaced apart from surface 52 of plate 30 to move driver from the first orientation to the second orientation, as discussed herein. In some embodiments, springs 152 extend parallel to axis X1, when sleeve 70 is positioned in passageway 28 and knob 130 is coupled to sleeve 70. In some embodiments, at least one of springs 152 may be disposed at alternate orientations, relative to axis X1, such as, for example, transverse and/or other angular orientations such as acute or obtuse, co-axial and/or may be offset or staggered.

Assembly 14 includes a shaft 194 that is coupled to sleeve 18 such that shaft 194 is coaxial with axis X1 and is permanently fixed relative to sleeve 18. That is, shaft 194 cannot be removed from sleeve 18 without breaking shaft 194 and/or sleeve 18. In some embodiments, shaft 194 is permanently fixed to sleeve 18 by welding shaft 194 to sleeve 18. Shaft 194 includes a proximal end 196 extending through an opening 199 in plate 32 and an opposite distal end 200 extending through bore 78 and passageway 28 such that a distal tip 202 of end 200 is distal to end surface 48. Tip 202 defines a bit, such as, for example, a drive that is configured for disposal in a correspondingly shaped socket 204 in a shank, such as, for example, a shaft 206 of bone screw 208 such that rotation of shaft 194 about axis X1 also rotates shaft 206 when tip 202 is disposed in socket 204. In some embodiments, tip 202 and socket each include a hexalobe geometry for a mating engagement therebetween. In some embodiments, tip 202 can alternatively include a cruciform, Phillips, square, hexagonal, polygonal, star cross sectional configuration for disposal in a correspondingly shaped socket 204.

End 196 includes a portion 198 configured to facilitate connection of driver 12 with a surgical instrument, such as, for example, an actuator/drill that is the same or similar to that disclosed in U.S. patent application Ser. No. 15/492,867, U.S. patent application Ser. No. 15/661,962 and/or U.S. patent application Ser. No. 15/661,986. In some embodiments, portion 198 includes quick connect surfaces or keyed geometry, such as, for example, triangle, hex, square or hexalobe to facilitate connection with the actuator/drill. End 196 further includes a portion 210 configured to facilitate connection of driver 12 with a navigation component, such as, for example, a navigation component that is the same or similar to that disclosed in U.S. patent application Ser. No. 15/492,867, U.S. patent application Ser. No. 15/661,962 and/or U.S. patent application Ser. No. 15/661,986 and is configured for operation with a navigation system that is the same or similar to that disclosed in U.S. patent application Ser. No. 15/492,867, U.S. patent application Ser. No. 15/661,962 and/or U.S. patent application Ser. No. 15/661,986.

Assembly 16 is configured to be removably coupled to assembly 14 and includes an outer sheath 212 including a body 213 extending along a central longitudinal axis X5 between a proximal end 214 and an opposite distal end 216. Sheath 212 includes an inner surface 218 defining a conduit 220. Sheath 212 includes a pair of opposing tabs 224, 226 extending outwardly from body 213 and distally from an end surface 228 of end 216. In some embodiments, tabs 224, 226 are fixed and/or permanently fixed relative to body 213 such that tabs 224, 226 cannot be removed from and/or moved relative to body 213 without breaking tabs 224, 226 and/or body 213. In some embodiments, tabs 224, 226 are integrally and/or monolithically formed with body 213. Tabs 224, 226 are each configured for disposal in recesses 42, 44 as assembly 16 is being connected with assembly 14 and/or for disposal between adjacent arms 230, 232 of a head or receiver 234 of bone screw 208 after assembly 16 is connected to assembly 14, as discussed herein. Accordingly, tabs 224, 226 each have a configuration, such as, for example, a size and shape that corresponds to and/or is complementary with configurations of recesses 42, 44 and the spaces between arms 230, 232.

Assembly 16 includes an inner sheath 236 rotatably positioned in conduit 220 such that a proximal end 238 of sheath 236 extends through end 214 and an opposite distal end 240 of sheath 236 extends through end 216. That is, end 238 projects proximally through end 214 such that end 238 is positioned proximal to end 214 and end 240 projects distally through end 216 such that end 240 is positioned distal to end 216. Shaft 194 is configured to be positioned in a pathway 270 of sheath 236 when assembly 16 is coupled to assembly 14, as discussed herein. End 238 includes a wall 242 having an outer surface 244 that defines a hexagonal configuration and is configured for disposal in hexagonal bore 78 or a hexagonal portion of bore 78 such that rotating sleeve 70 relative to sleeve 18 about axis X1 also rotates sheath 236 relative to sleeve 18 about axis X1, as discussed herein. End 238 further includes a circumferential flange 246 that is spaced apart from wall 242 by a recess 248. That is, recess 248 is positioned between flange 246 and wall 242. In some embodiments, an outer surface of flange 246 defines a ramp 250 that is configured to slide along a ramp 252 of tab 94 and a ramp 254 of tab 106 as assembly 16 is being coupled to assembly 14, as discussed herein.

Figure 30:
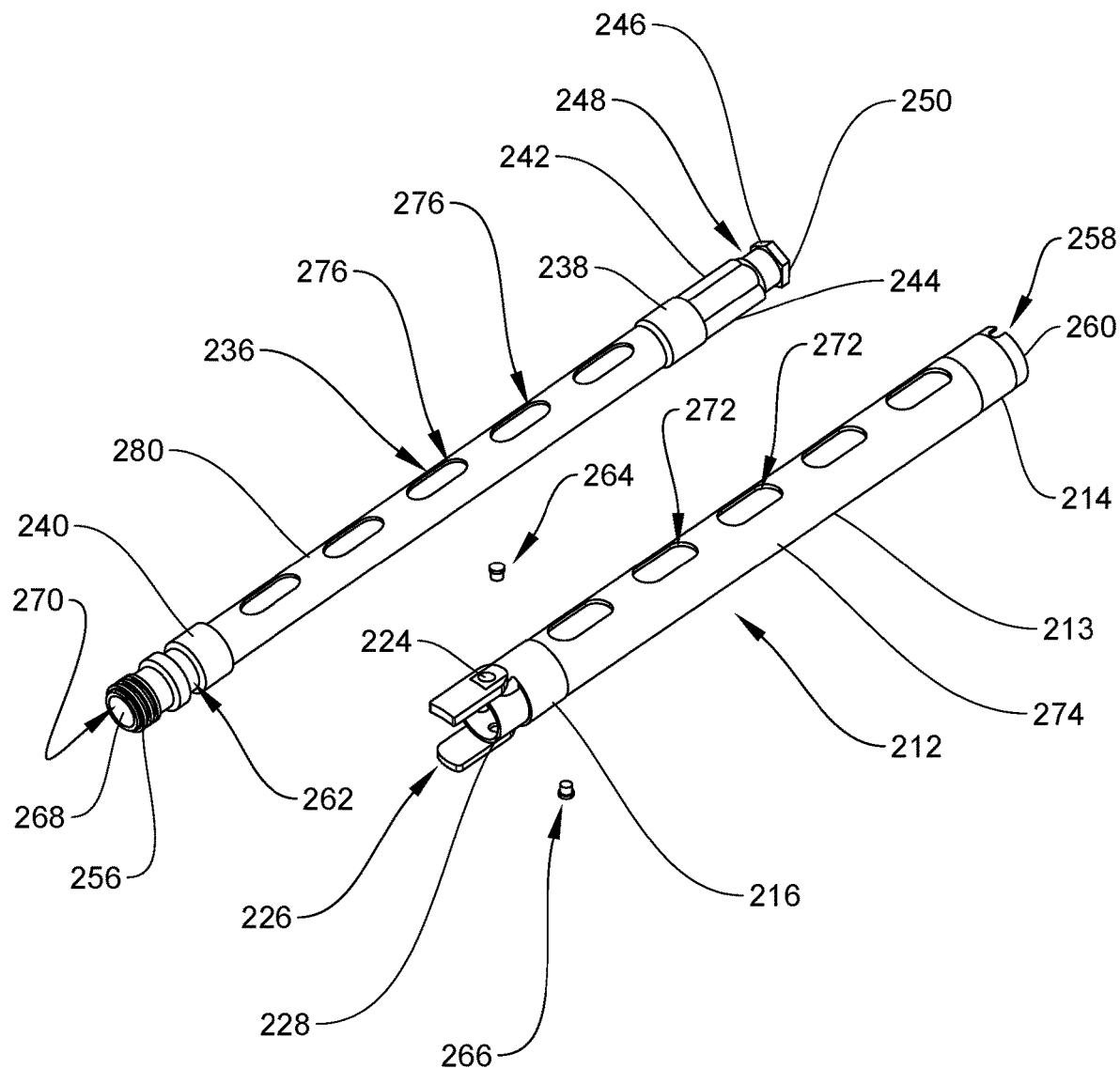
FIG. 30 is a perspective view of components of the surgical instrument shown in FIG. 1.

End 240 includes a threaded outer surface 256 configured to mate with a threaded inner surface of arm 230 and a threaded inner surface of arm 232 to couple assembly 16 to receiver 234, as discussed herein. In particular, driver 12 is coupled to bone screw 208 by inserting tip 202 into socket 204 to prevent relative rotation between shaft 194 of assembly 14 and shaft 206 of bone screw 208 while simultaneously positioning tabs 224, 226 between arms 230, 232 to prevent relative rotation between assembly 16 and receiver 234. Sheath 236 is then rotated relative to sheath 212 about axis X5 via rotation of knob 130 and hence sleeve 70 relative to sleeve 18 about axis X1 to mate threaded outer surface 256 with the threaded inner surfaces of arms 230, 232 to couple assembly 16 with receiver 234. In some embodiments, sheath 212 includes a notch 258 extending into a proximal end surface 260 of end 214, as shown in FIG. 30, for example. Notch 258 is configured to be aligned with one or more of tabs 224, 226 to engage receiver 234. For example, in some embodiments, notch 258 can be used as a visual indicator of how a rod slot defined by a space between arms 230, 232 is aligned and/or can aid in positioning bone screw 208. For example, notch 258 can allow a medical practitioner to know that tabs 224, 226 are aligned with the spaces between arms 230, 232 without being able to directly see bone screw 208. In some embodiments, sheath 212 includes only one notch 258. In some embodiments, sheath 212 includes a plurality of notches 258. In some embodiments, sheath 212 includes two notches 258 positioned opposite one another such that one of notches 258 is aligned with tab 224 and the other notch 258 is aligned with tab 226. In some embodiments, at least one notches 258 extends parallel to axis X5. In some embodiments, at least one notches 258 may be disposed at alternate orientations, relative to axis X5, such as, for example, transverse, perpendicular and/or other angular orientations such as acute or obtuse, co-axial and/or may be offset or staggered. In some embodiments, at least one notches 258 is variously shaped, such as, for example, rectangular, circular, oval, oblong, triangular, square, polygonal, irregular, uniform, non-uniform, offset, staggered, undulating, arcuate, variable and/or tapered.

Sheath 236 is rotatable relative to sheath 212, as discussed herein. In some embodiments, end 240 of sheath 236 includes a circumferential groove 262 extending into an outer surface of sheath 236. Spaced apart pins 264, 266 each extend through sheath 212 and into groove 262 such that pins 264, 266 are positioned in groove 262 to prevent sheath 236 from translating relative to sheath 212 along axis X5, while allowing rotation of sheath 236 relative to sheath 212 about axis X5. In some embodiments, pin 264 extends through tab 224 and body 213 and into groove 262 and pin 266 extends through tab 226 and body 213 and into groove 262.

Sheath 236 includes an inner surface 268 that defines pathway 270. Shaft 194 is rotatably disposed in pathway 270 when assembly 16 is coupled to assembly 14, as discussed herein. In some embodiments, pathway 270 may have various cross section configurations, such as, for example, oval, oblong, triangular, rectangular, square, polygonal, irregular, uniform, non-uniform, variable, tubular and/or tapered. In some embodiments, pathway 270 may be disposed at alternate orientations, relative to axis X5, such as, for example, parallel, transverse and/or other angular orientations such as acute or obtuse, co-axial and/or may be offset or staggered.

Figure 29:
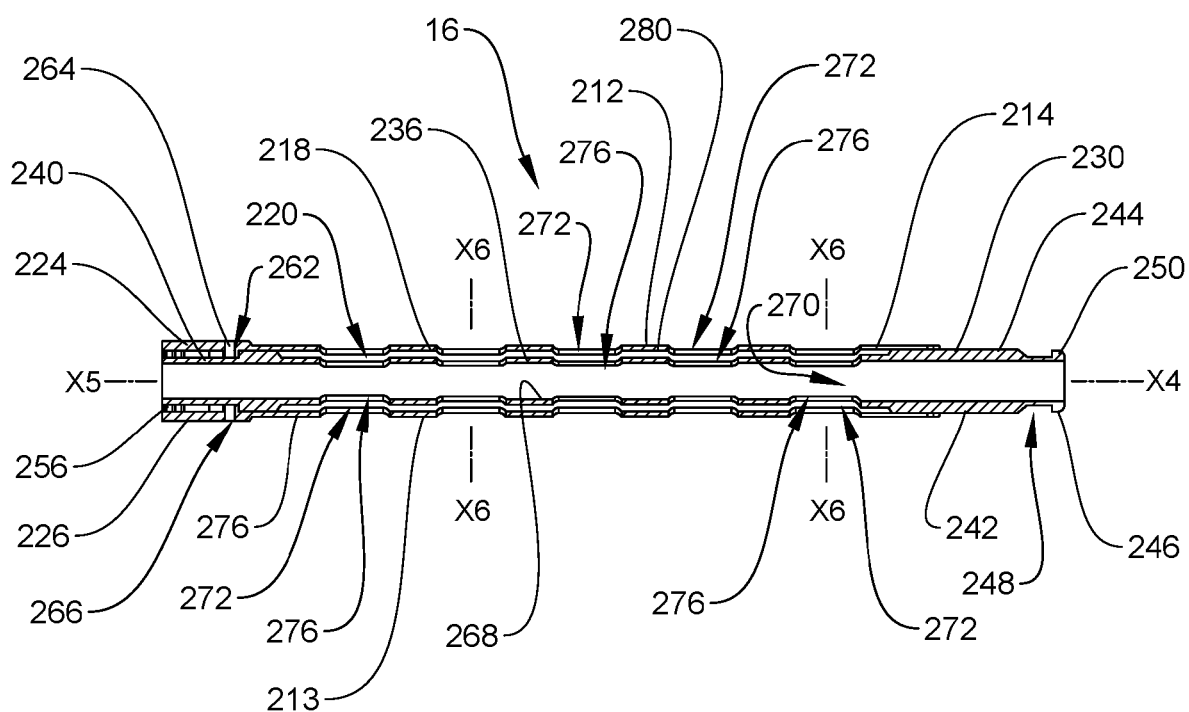
FIG. 29 is a side, cross-sectional view of components of the surgical instrument shown in FIG. 1.

In some embodiments, sheath 212 includes one or a plurality of slots 272 each extending through surface 218 and an opposite outer surface 274 of sheath 212 and/or sheath 236 includes one or a plurality of slots 276 each extending through surface 268 of sheath 236 and an opposite outer surface 280 of sheath 236. Each of slots 276 is aligned with one of slots 272 when sheath 236 is coupled to sheath 212 such that pins 264, 266 are disposed in groove 262, as discussed herein. In embodiments wherein sheath 212 includes a plurality of slots 272, slots 272 are spaced apart from one another. In some embodiments wherein sheath 212 includes a plurality of slots 272, slots 272 extend parallel to axis X5 and are disposed in a serial configuration along axis X5. For example, in some embodiments, slots 272 are arranged in one or more columns that each extend parallel to axis X5. In some embodiments, sheath 212 includes three or more columns of slots 272, wherein the columns are uniformly spaced apart about axis X5. In some embodiments, sheath 212 includes two opposing columns of slots 272 such that each of the slots 272 in one column is aligned with one of the slots 272 in the other column along an axis X6 that extends perpendicular to axis X5, as can be seen in FIG. 29, for example. In embodiments wherein sheath 236 includes a plurality of slots 276, slots 276 are spaced apart from one another. In some embodiments wherein sheath 236 includes a plurality of slots 276, slots 276 extend parallel to axis X5 and are disposed in a serial configuration along axis X5. For example, in some embodiments, slots 276 are arranged in one or more columns that each extend parallel to axis X5. In some embodiments, sheath 236 includes three or more columns of slots 276, wherein the columns are uniformly spaced apart about axis X5. In some embodiments, sheath 236 includes two opposing columns of slots 276 such that each of the slots 276 in one column is aligned with one of the slots 276 in the other column along axis X6, as can be seen in FIG. 29, for example. It is envisioned that slots 272 and/or slots 276 may be useful for cleaning driver 12 and/or visualizing components of driver 12 or another instrument within conduit 220 and/or pathway 270. In some embodiments, slots 272 and/or slots 276 may be variously shaped, such as, for example, circular, oval, oblong, triangular, square, polygonal, irregular, uniform, non-uniform, offset, staggered, undulating, arcuate, variable and/or tapered. In some embodiments, at least one of slots 276 is aligned with one of slots 272 and one of slots 50 to allow simultaneous visualization through slots 50, 272, 276. That is, when driver 12 is in the first orientation in which assembly 16 is coupled to assembly 14 in a manner that prevents assembly 16 from translating relative to assembly 14, each of slots 50 is aligned with one of slots 272 and one of slots 276.

Figure 7:
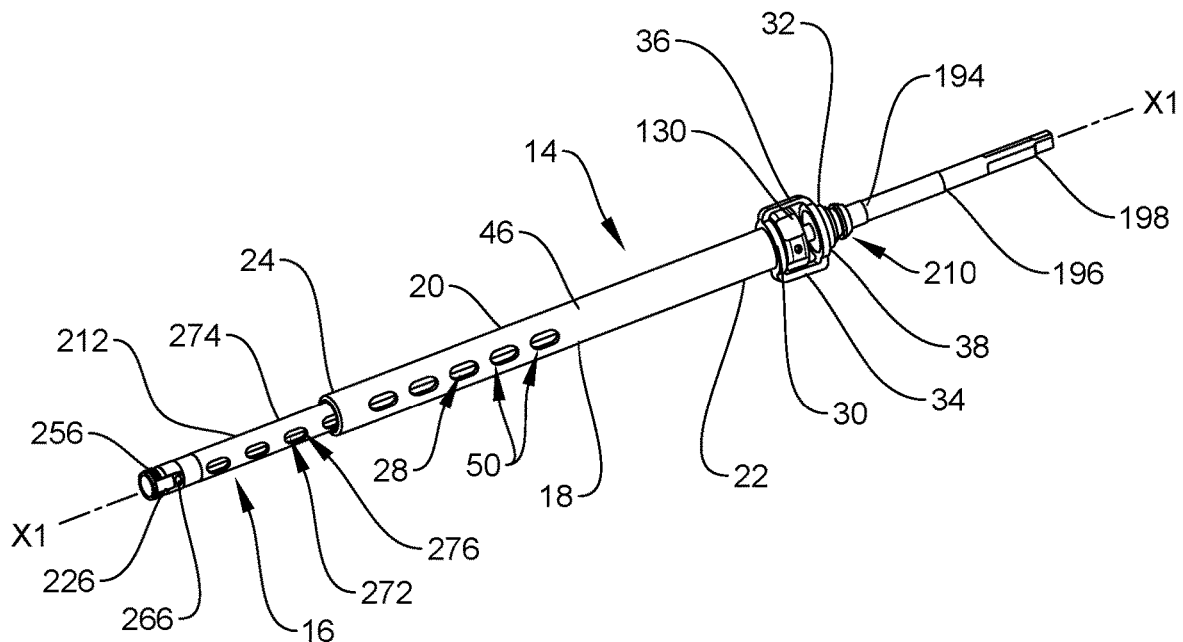
FIG. 7 is a perspective view of components of the surgical instrument shown in FIG. 1.
Figure 8:
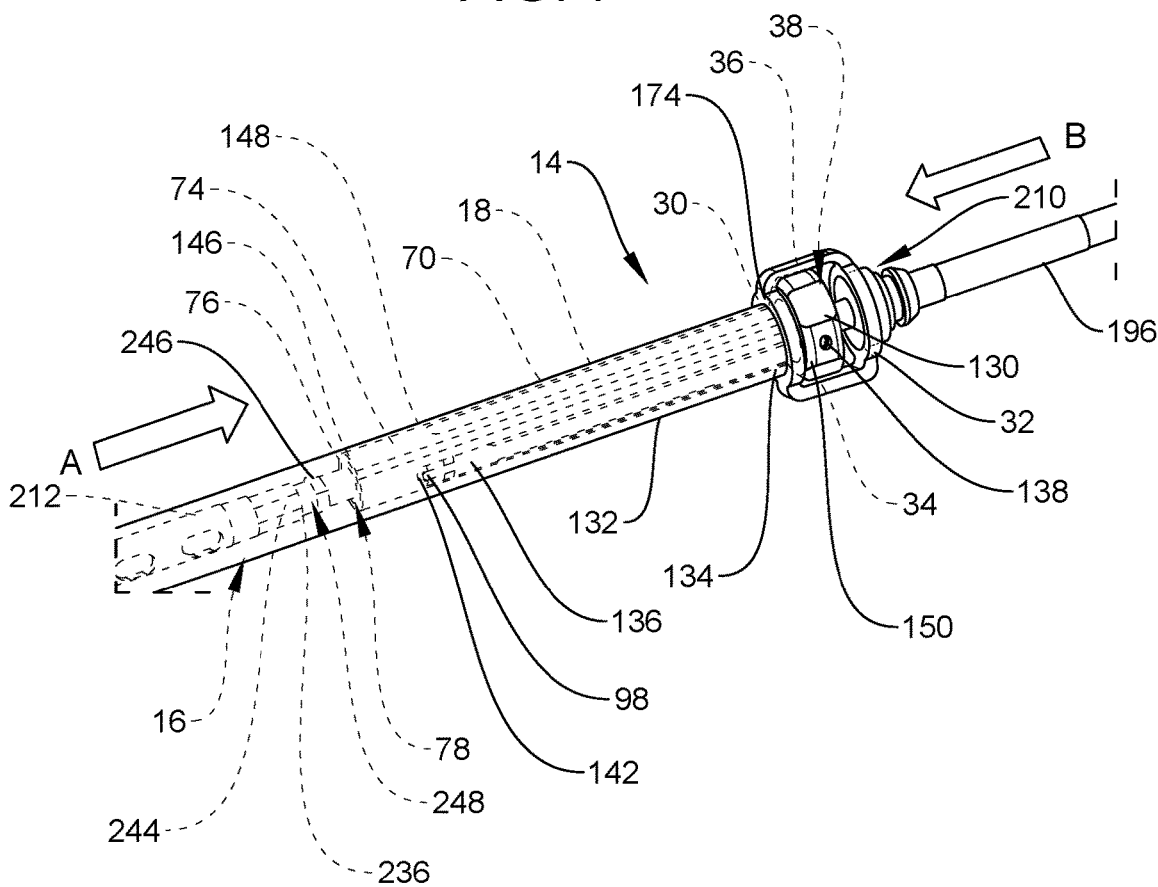
FIG. 8 is a perspective view of components of the surgical instrument shown in FIG. 1.
Figure 9:
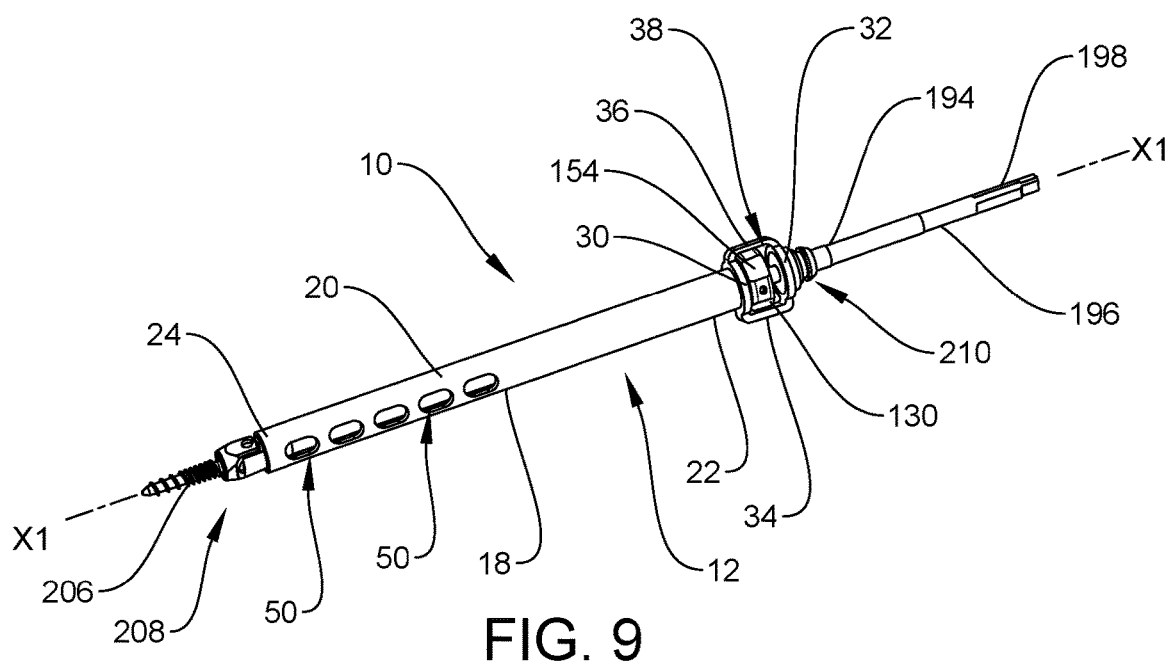
FIG. 9 is a perspective view of components of the surgical instrument shown in FIG. 1.

In some embodiments, assembly 16 is connected to assembly 14 to dispose driver 12 in the first orientation, as discussed herein. In particular, driver 12 moves from an unassembled configuration in which assembly 16 is disconnected from assembly 14 to an assembled configuration in which driver 12 is in the first orientation discussed herein by inserting end 238 of sheath 236 into passageway 28 with sheath 236 rotatably disposed in sheath 212, as discussed herein, as shown in FIG. 7, for example. Assembly 16 is translated proximally relative to assembly 14 along axis X1 (in the direction shown by arrow A in FIG. 8) such that shaft 194 is positioned in pathway 270 of sheath 236, as shown in FIG. 8, for example. In some embodiments, assembly 16 is translated proximally relative to assembly 14 by pushing assembly 16 from distal end 216 of sheath 212 and/or distal end 240 of sheath 236 proximally (in the direction shown by arrow A in FIG. 8) and pushing surface 156 of knob 130 distally (in the direction shown by arrow B in FIG. 8).

Figure 10:
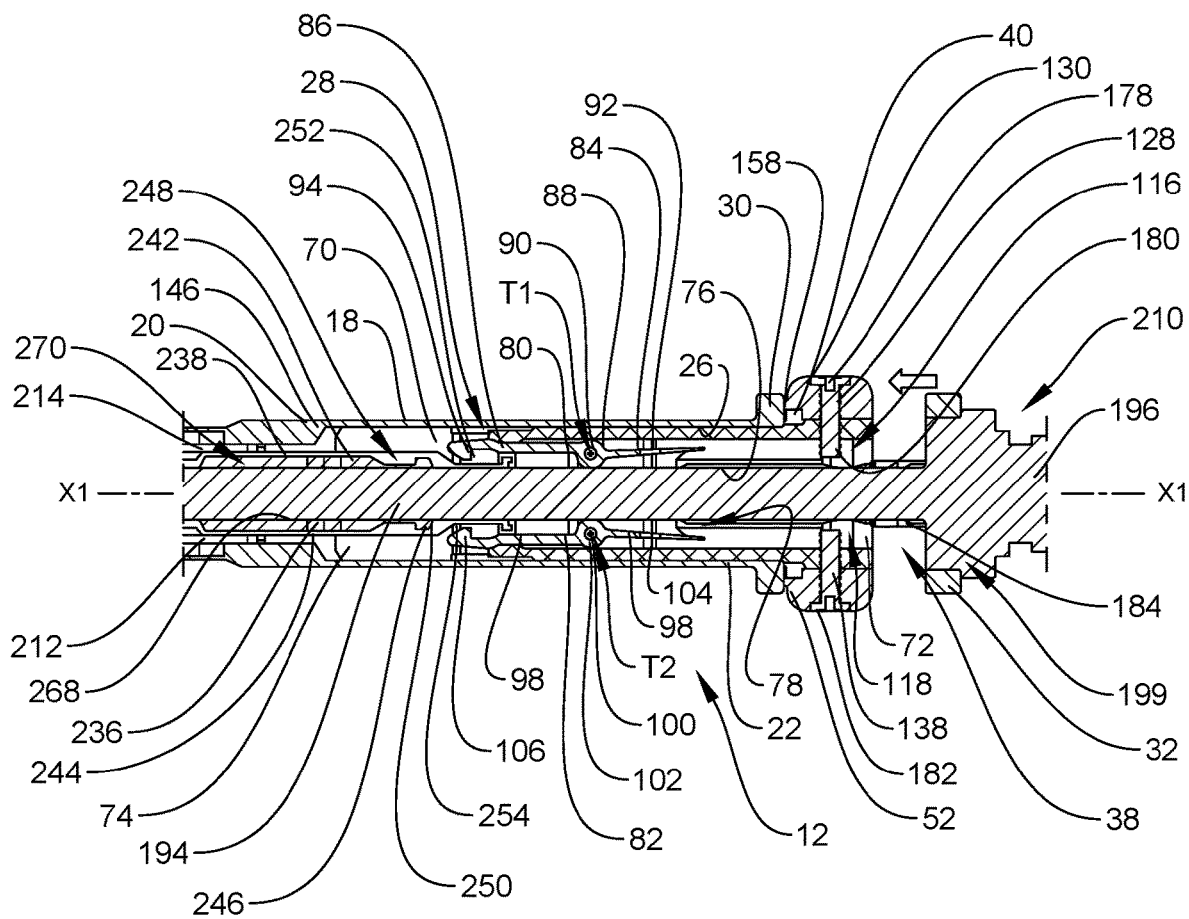
FIG. 10 is a side, cross-sectional view of components of the surgical instrument shown in FIG. 1.
Figure 12:
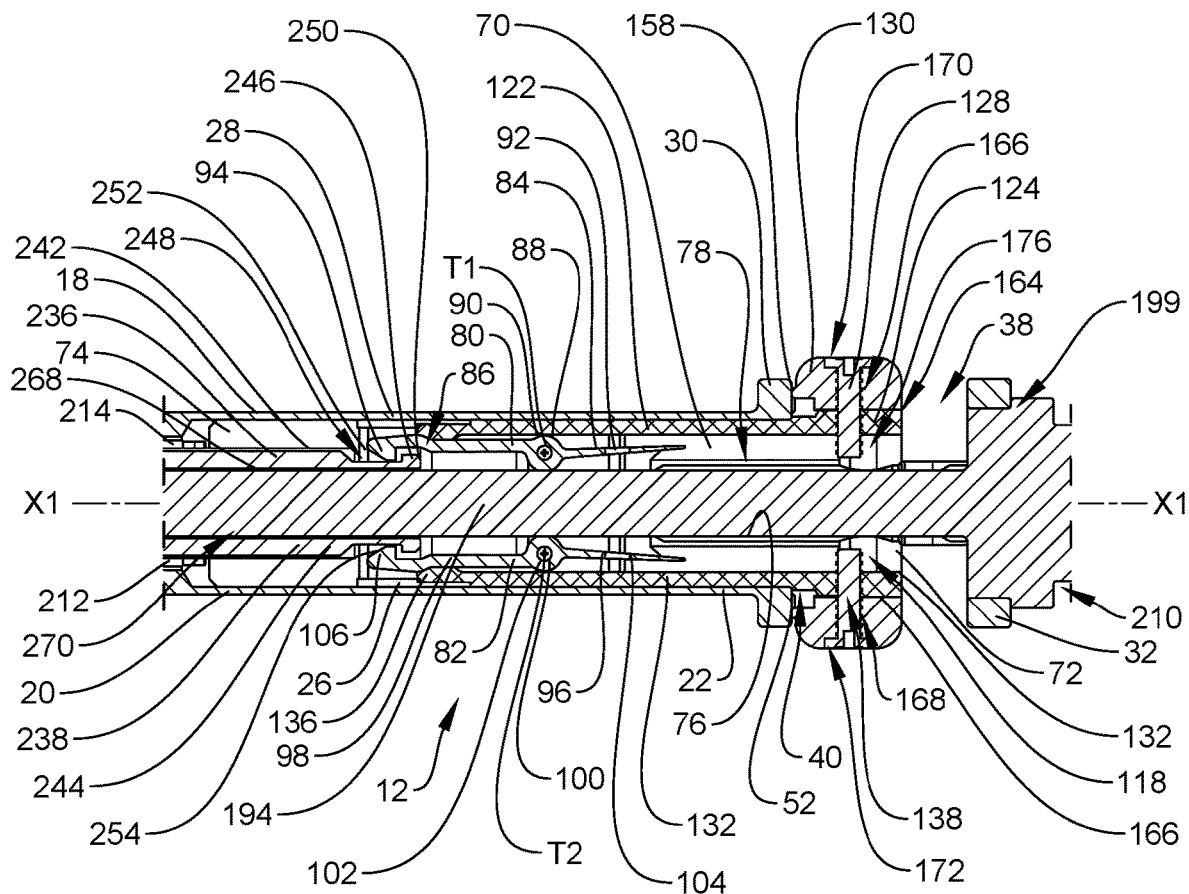
FIG. 12 is a side, cross-sectional view of components of the surgical instrument shown in FIG. 1.
Figure 13:
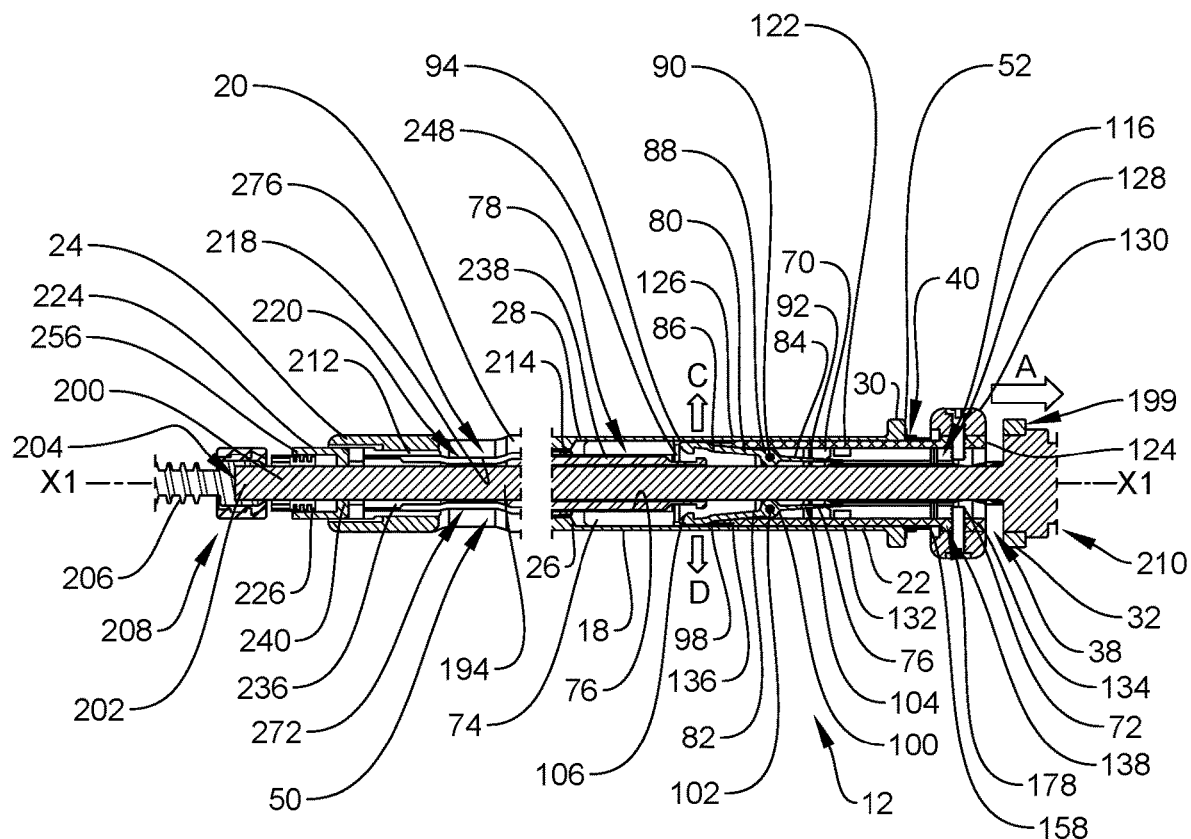
FIG. 13 is a side, cross-sectional view of components of the surgical instrument shown in FIG. 1 and the implant shown in FIG. 5.
Figure 14:
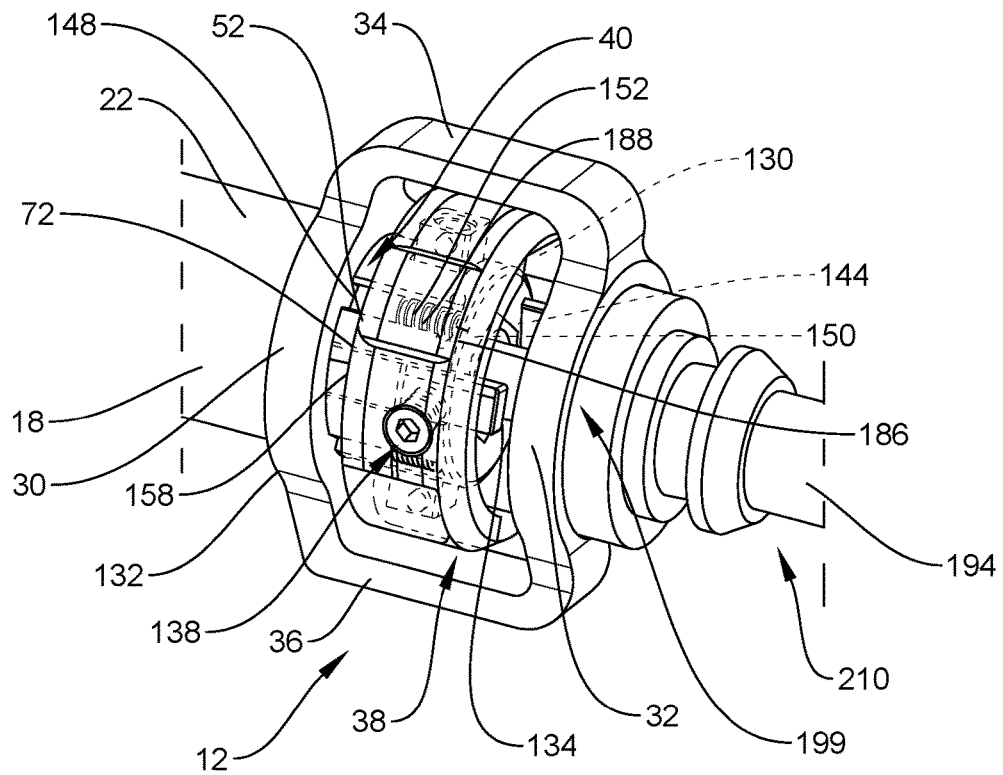
FIG. 14 is a perspective view, in part phantom, of components of the surgical instrument shown in FIG. 1.

Assembly 16 is further translated proximally relative to assembly 14 along axis X1 (in the direction shown by arrow A in FIG. 8) such that the hexagonal portion of wall 242 is inserted into and/or engages hexagonal bore 78 or a portion of surface 76 that defines the hexagonal portion of bore 78, as shown in FIG. 10, for example, such that rotating sleeve 70 relative to sleeve 18 about axis X1 also rotates sheath 236 relative to sleeve 18 about axis X1, as discussed herein. As assembly 16 translates proximally relative to assembly 14 along axis X1 (in the direction shown by arrow A in FIG. 8), tab 224 is inserted into and slides along recess 42 and tab 226 is inserted into and slides along recess 44, as can be seen in FIGS. 4 and 11, for example. Assembly 16 is further translated proximally relative to assembly 14 along axis X1 (in the direction shown by arrow A in FIG. 8) such that ramps 252, 254 of tabs 94, 106 slide along ramp 250 of flange 246 of sheath 236. The sliding of ramps 252, 254 along ramp 250 causes latch 80 to pivot about axis T1 and latch 82 to pivot about axis T2 to allow flange 246 to be positioned proximally relative tabs 94, 106 along axis X1 such that tabs 94, 106 are aligned with groove recess 248, as shown in FIG. 13. As latch 80 pivots about axis T1 and latch 82 pivots relative to axis T2, tab 94 moves in the shown by arrow C in FIG. 13 and tab 106 moves in the direction shown by arrow D in FIG. 13. Leaf springs 92, 104 then cause latch 80 to pivot relative to axis T1 and latch 82 to pivot relative to axis T2 to move tabs 94, 106 into recess 248, as shown in FIG. 12, to prevent assembly 16 from translating relative to assembly 14 in opposite directions along axis X1. In particular, leaf springs 92, 104 cause latch 80 to pivot relative to axis T1 and latch 82 to pivot relative to axis T2 such that tab 94 moves in the direction shown by arrow D in FIG. 13 and tab 106 moves in the direction shown by arrow C in FIG. 13. When tabs 94, 106 are disposed in recess 248 in a manner that prevents assembly 16 from translating relative to assembly 14 in opposite directions along axis X1, driver 12 is in the first orientation.

To move driver 12 from the first orientation, in which assembly 16 is prevented from translating relative to assembly 14 in opposite directions along axis X1, to the second orientation, in which assembly 16 is able to translate relative to assembly 14 in opposite directions along axis X1, the surgeon moves knob 130 proximally (in the direction shown by arrow A in FIG. 13) relative to sleeve 70 such that pin 128 translates proximally within slot 116 and pin 138 translates proximally within slot 118. As pin 128 translates proximally within slot 116, lever 122 translates proximally relative to sleeve 70 to pivot latch 80 such that tab 94 moves in the direction shown by arrow C in FIG. 13. Likewise, as pin 138 translates proximally within slot 118, lever 132 translates proximally relative to sleeve 70 to pivot latch 82 such that tab 106 moves in the direction shown by arrow D in FIG. 13. That is, tab 94 moves in the direction shown by arrow C in FIG. 13 and tab 106 moves in the direction shown by arrow D in FIG. 13 to move tabs 94, 106 out of recess 248 and allow assembly 16 to translate relative to assembly 14 in opposite directions along axis X1. When assembly 16 is inserted into assembly 14 and assembly 16 is configured to translate relative to assembly 14 in opposite directions along axis X1, driver 12 is in the second orientation.

Figure 31:
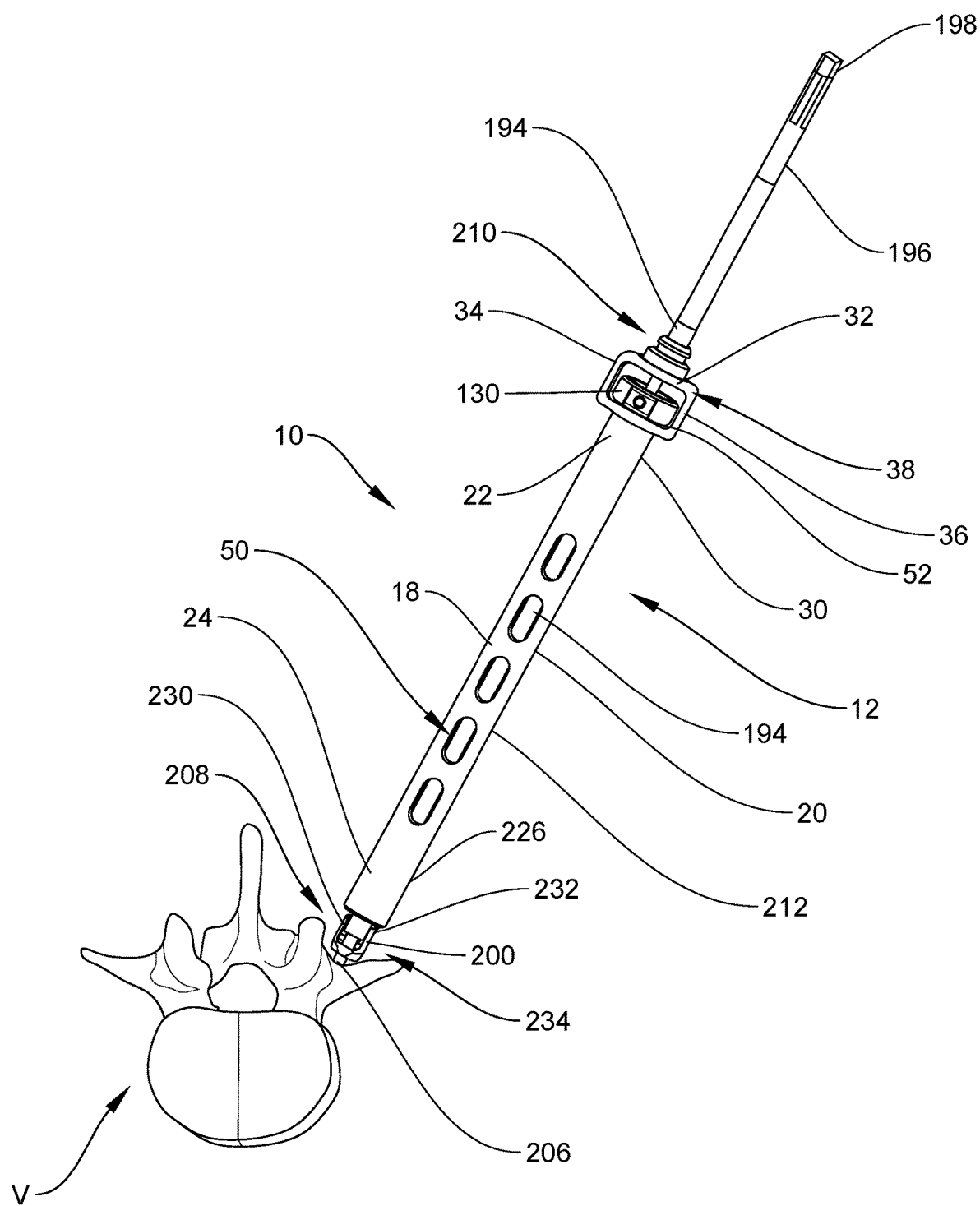
FIG. 31 is a plan view of the surgical instrument shown in FIG. 1 and the implant shown in FIG. 5.
Figure 32:
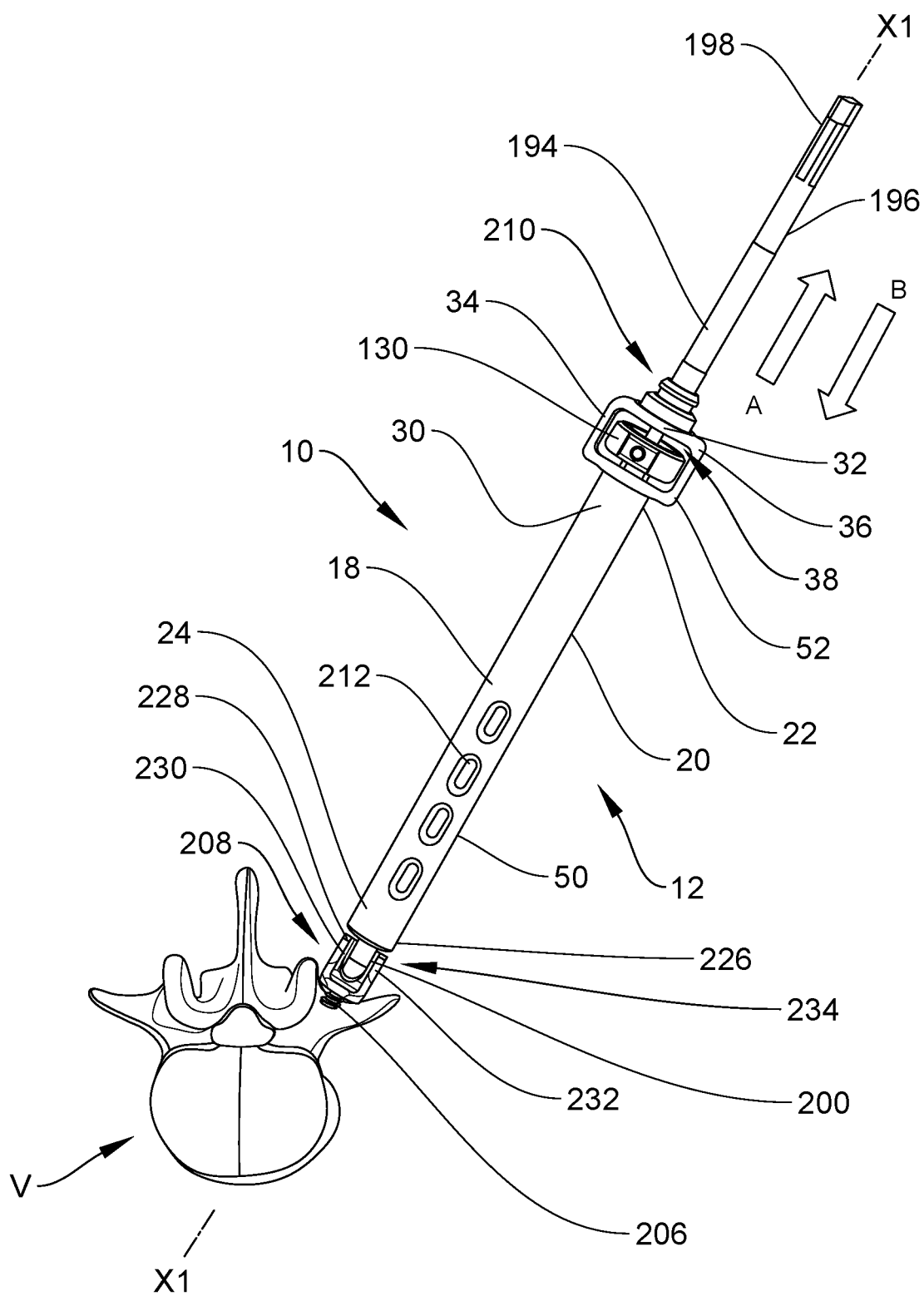
FIG. 32 is a plan view of the surgical instrument shown in FIG. 1 and the implant shown in FIG. 5.
Figure 33:
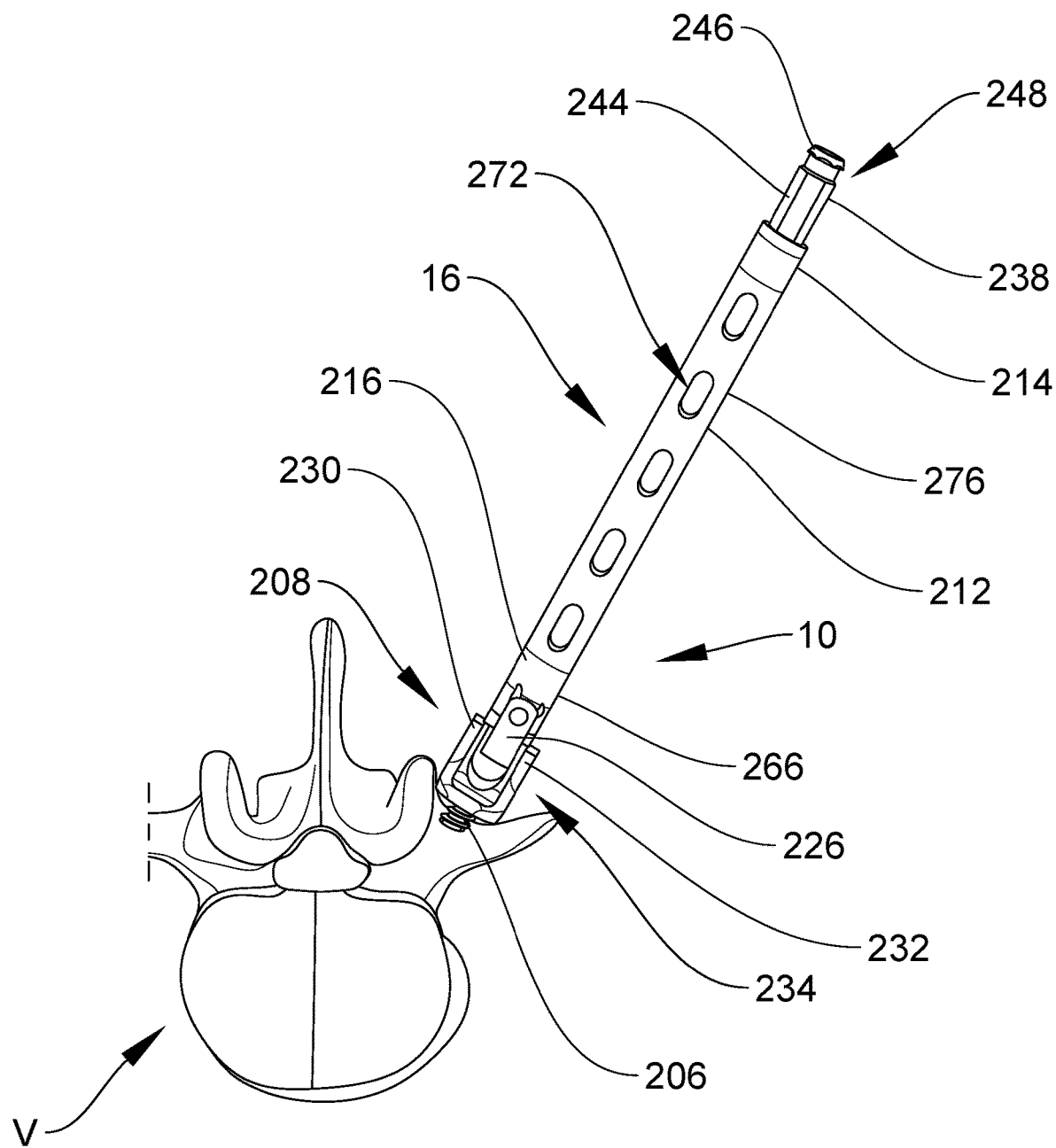
FIG. 33 is a plan view of components of the surgical instrument shown in FIG. 1 and the implant shown in FIG. 5.
Figure 34:
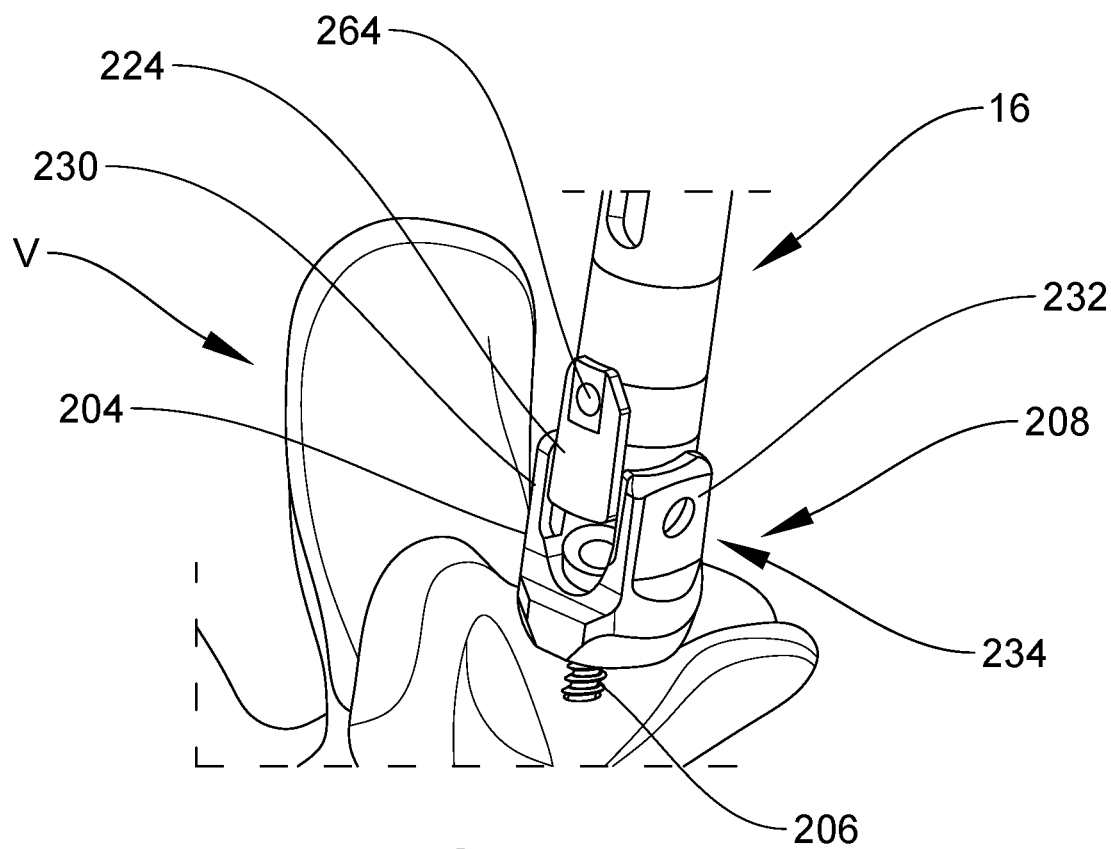
FIG. 34 is a close-up, plan view of components of the surgical instrument shown in FIG. 1 and the implant shown in FIG. 5.

In use, bone screw 208 is connected with driver 12, as shown in FIG. 31, for example. In particular, bone screw 208 is connected with driver 12 when driver 12 is in the first orientation, in which assembly 16 is inserted into assembly 14 and is prevented from translating relative to sleeve 18 along axis X1, as shown in FIG. 12, for example. In particular, bone screw 208 is connected with driver 12 by inserting tip 202 into socket 204 such that threaded surface 256 of sheath 212 is aligned with threaded surfaces of arms 230, 232 and tabs 224, 226 are positioned between arms 230, 232. Knob 130 is rotated relative to sleeve 18 about axis X1 to rotate assembly 16 to mate threaded surface 256 with the threaded surfaces of arms 230, 232 and couple assembly 16 with receiver 234. Driver 12 is then rotated about axis X1 to simultaneously rotate receiver 234 and shaft 206 about axis X1 and drive shaft 206 into tissue, such as, for example, bone. Assembly 14 may then be moved from bone screw 208 by moving driver 12 from the first orientation shown in FIG. 12, in which assembly 16 is prevented from translating relative to sleeve 18 along axis X1, to the second orientation shown in FIG. 13, in which assembly 16 is capable of translating relative to sleeve 18 along axis X1 by moving knob 130 in the direction shown by arrow A in FIG. 32, as discussed herein. Once driver 12 is in the second orientation, assembly 14 can be disengaged from bone screw 208 by moving assembly 14 proximally relative to assembly 16 to disengage assembly 14 from bone screw 208, while leaving assembly 16 coupled to bone screw 208, as shown in FIGS. 33 and 34.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. For example, in some embodiments, driver 12 may be delivered with driver 12 in the first orientation, in which assembly 16 is coupled to assembly 14 such that assembly 16 is prevented from translating relative to assembly 14 about axis X1. In some embodiments, driver 12 may be delivered with driver 12 in the second orientation, in which assembly 16 is capable of translating relative to sleeve 18 along axis X1. Spinal implant system 10 may be completely or partially revised, removed or replaced.

In use, to treat one or more vertebrae, such as, for example, vertebra V1 shown in FIGS. 31-34, a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

A pilot hole (not shown) is made in vertebra V1 for receiving shaft 206 of bone screw 208. Bone screw 208 is connected with driver 12, as described herein, and shown in FIG. 31, for example. In some embodiments, an actuator, such as, for example, a drill is coupled to portion 198 of shaft 194 to rotate driver 12 relative to vertebra V1 about axis X1 such that assembly 16, sleeve 18, sleeve 70 and shaft 194 rotate relative to vertebra V1 about axis X1. Rotation of driver 12 about axis X1 relative to vertebra V1 engages one or more threads of shaft 206 with vertebra V1 to fix shaft 206 relative to vertebra V1.

Once shaft 206 is sufficiently driven into vertebra V1 using driver 12, assembly 14 may be removed from bone screw 208, while leaving assembly 16 attached to receiver 234 of bone screw 208, as discussed herein. In particular, the surgeon may grasp knob 130 by hand and translate knob 130 relative to sleeve 18 and sleeve 70 along axis X1 in the direction shown by arrow A in FIG. 32 while pulling back on sleeve 18 in the direction shown by arrow B in FIG. 32 to move driver 12 from the first orientation, in which assembly 16 is prevented from translating relative to sleeve 18 along axis X1, to the second orientation, in which assembly 16 is able to translate relative to sleeve 18 in opposite directions along axis X1. With driver 12 in the second orientation, assembly 14 is translated relative to assembly 16 and bone screw 208 in the direction shown by arrow A in FIG. 32, leaving assembly 16 coupled to receiver 234 of bone screw 208, as shown in FIGS. 33 and 34. In some embodiments, the surgeon may utilize assembly 16 to guide other instruments, for example, to bone screw 208.

Figure 35:
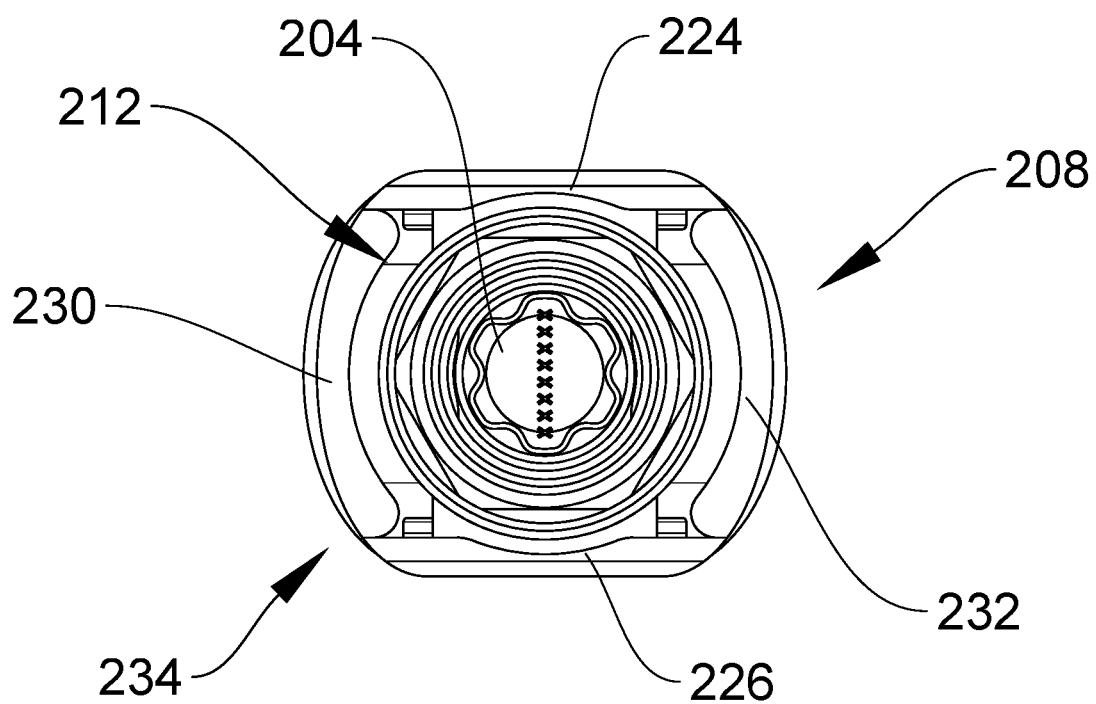
FIG. 35 is a top view of components of the surgical instrument shown in FIG. 1 and the implant shown in FIG. 5.

In some embodiments, assembly 16 is coupled to receiver 234 such that the maximum outside diameter of sheath 212 of assembly 16 is smaller than the head of the screw and smaller than the maximum outside diameter of receiver 234, as shown in FIG. 35. The maximum outside diameter of sheath 212 is also smaller than the engagement slots of receiver 234 defined by the space between arms 230, 232. This allows instruments to slide down assembly 16 and engage with those features so as to lock onto receiver 234.

Figure 36:
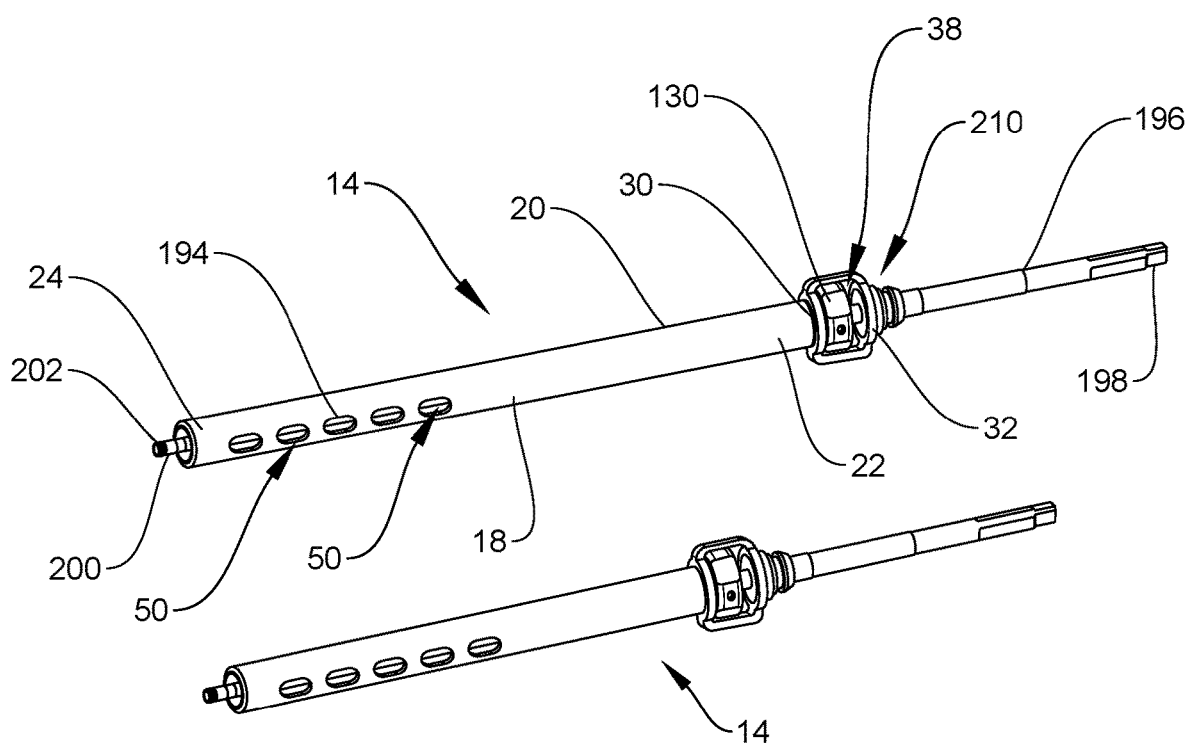
FIG. 36 is a perspective view of components of the system.
Figure 37:
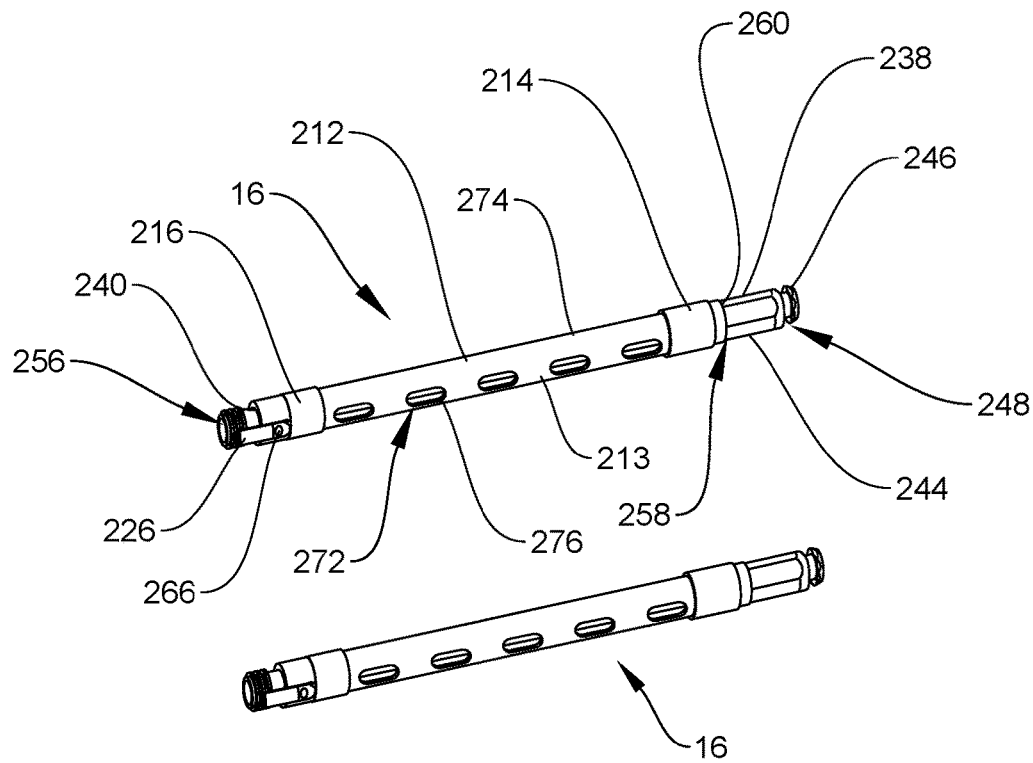
FIG. 37 is a perspective view of components of the system.

In some embodiments, driver 12 can be configured to have a selected length, for example. That is, the length of driver 12 can be adjusted (shortened and lengthened) for use with a particular procedure. As such, in some embodiments, system 10 includes outer assemblies 14 having different lengths, as shown in FIG. 36 and/or inner assemblies 16 having different lengths, as shown in FIG. 37. It is envisioned that each of the inner assemblies 16 shown in FIG. 37 can be used with each of the outer assemblies 14 shown in FIG. 36 to allow the components shown in FIGS. 36 and 37 to be assembled with one another in a manner that results in a plurality of different length drivers 12.

Figure 38:
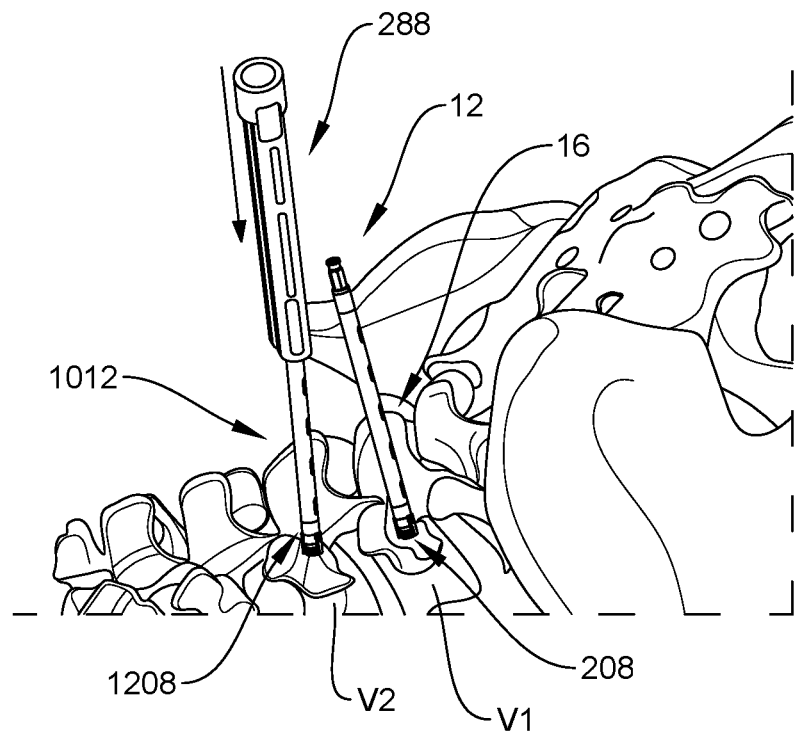
FIG. 38 is plan view of a component of the surgical instrument shown in FIG. 1 and a component of a second one of the surgical instruments shown in FIG. 1 coupled to a portion of an additional surgical instrument in accordance with the principles of the present disclosure.
Figure 39:
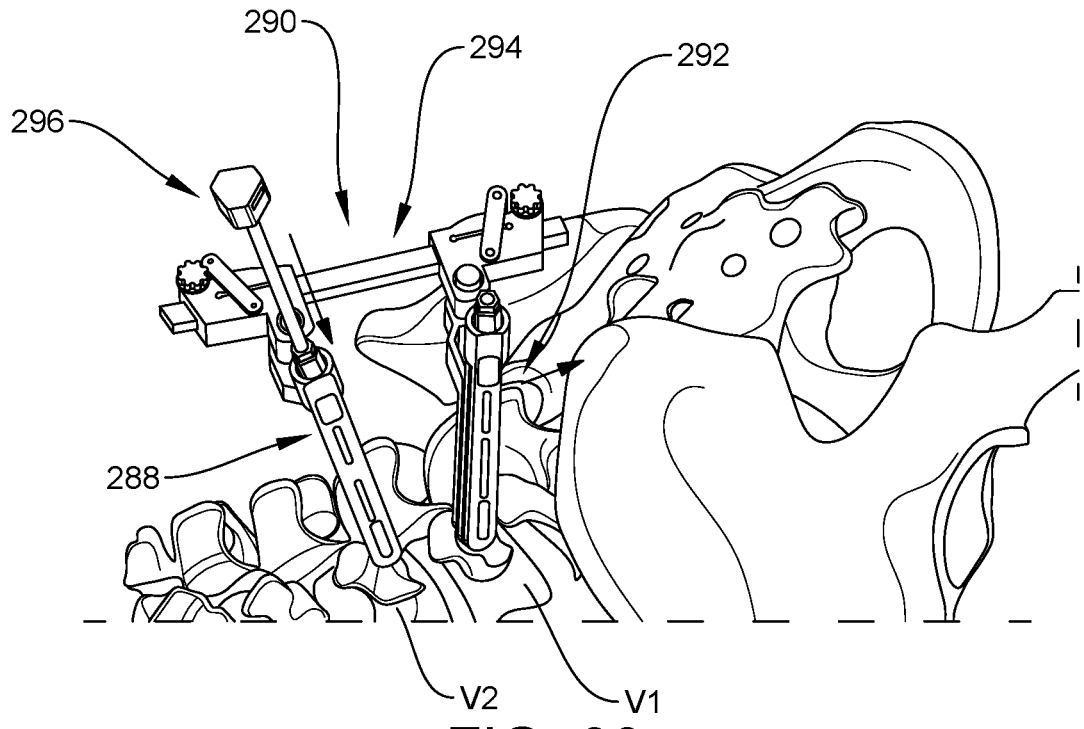
FIG. 39 is plan view of a component of the surgical instrument shown in FIG. 1 coupled to a component of the additional surgical instrument and a component of the second one of the surgical instruments shown in FIG. 1 coupled to the portion of the additional surgical instrument.
Figure 39A:
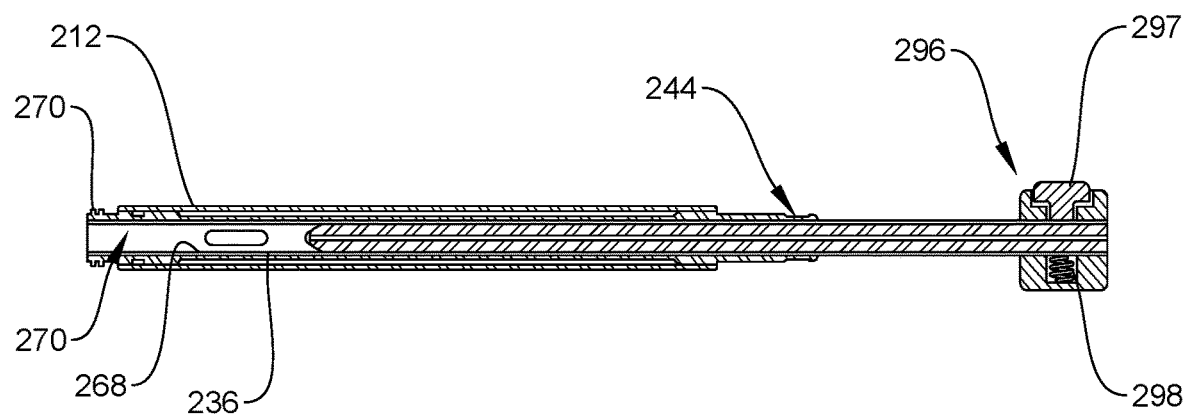
FIG. 39A is plan view of a component of the surgical instrument shown in FIG. 1 coupled to a component of the additional surgical instrument.
Figure 39B:
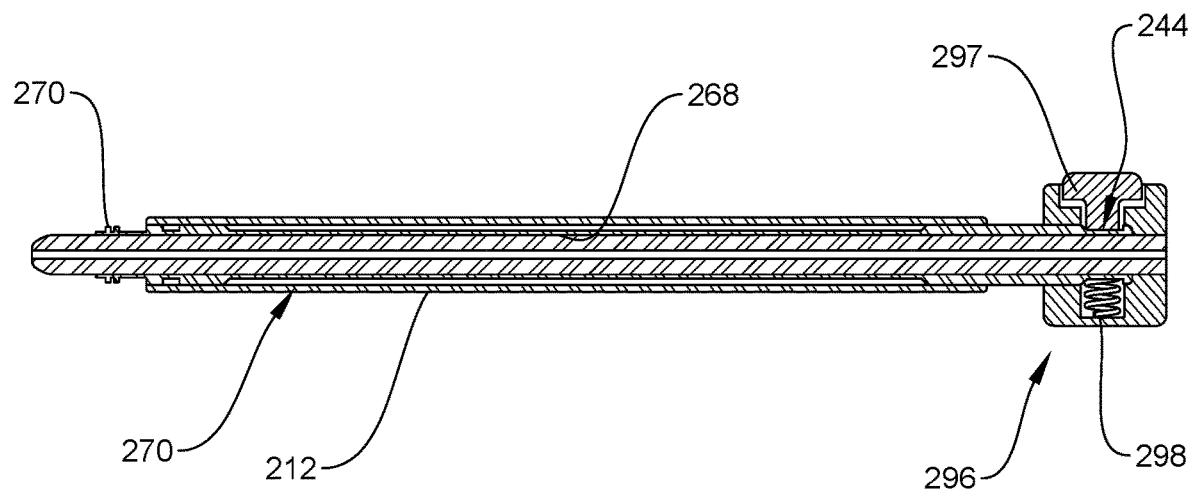
FIG. 39B is plan view of a component of the surgical instrument shown in FIG. 1 coupled to a component of the additional surgical instrument.

In some embodiments, driver 12 is used to drive bone screw 208 into vertebra V1, while retaining assembly 16 coupled to bone screw 208 after assembly 14 has been removed from bone screw 208, and while another driver 1012, that is the same or similar to driver 12 is used to drive another bone screw 1208, that is the same or similar to bone screw 208, into a vertebra V2 that is adjacent to vertebra V1 in a patient's vertebrae, as shown in FIG. 38. In particular, driver 1012 may be used to drive bone screw 1208 into vertebra V2, while leaving assembly 16 coupled to bone screw 1208 after assembly 14 has been removed from assembly 16 in the same manner that driver 12 is used to drive bone screw 208 into vertebra V1, while leaving assembly 16 coupled to bone screw 208 after assembly 14 has been removed from assembly 16. A component of another instrument of system 10, such as, for example, a first tower 288 of an instrument 290 may be translated over assembly 16 of driver 1012, while assembly 16 of driver 1012 is coupled to bone screw 1208, as shown in FIG. 38. A second tower 292 of instrument 290 is translated over assembly 16 of driver 12, while assembly 16 of driver 12 is coupled to bone screw 208, as shown in FIG. 39. Tower 292 is coupled to tower 292 by a member 294 that allows relative movement between tower 288 and tower 292 and to maintain towers 288, 292 in place to selectively position tower 288 relative to tower 292. In some embodiments, assembly 16 of driver 1012 is coaxial with tower 288 and assembly 16 of driver 12 is coaxial with tower 292.

Tower 292 may be moved apart from tower 288 to create a working space for a give surgical procedure. A head locker 296 may be inserted through pathway 270 of driver 1012, as shown in FIG. 39, and/or the same or different head locker 296 may be inserted through pathway 270 of driver 12 to maintain the relative positioning of shaft 206 of bone screw 1208 relative to receiver 234 of bone screw 1208 and/or the relative positioning of shaft 206 of bone screw 208 relative to receiver 234 of bone screw 208 and create a rigid construction. In some embodiments, head locker 296 engages assembly 16 of driver 1012 such that threads of head locker 296 engage threads of assembly 16 of driver 1012 to couple head locker 296 to driver 1012 and/or head locker 296 engages assembly 16 of driver 12 such that threads of head locker 296 engage threads of assembly 16 of driver 12 to couple head locker 296 to driver 12. In some embodiments, head locker 296 disengages assembly 16 of driver 1012 by pressing a button 297 on head locker 296 to uncouple head locker 296 from driver 1012 and/or head locker 296 disengages assembly 16 of driver 12 by pressing button 297 to uncouple head locker 296 from driver 12. In particular, head locker 296 is introduced into assembly 16 from the proximal end and button 297 causes a spring 298 to move into recess 248. When button 297 is pushed in, spring 298 is spaced apart from recess 248 and head locker 296 can be released from assembly 16. Head locker 296 is biased to a locked position when any force that was applied to button 297 is released such spring 298 moves into recess 248 to prevent head locker 296 from being released from assembly 16. In some embodiments, head locker 296 includes a wall having a hexagonal configuration that engages a portion of assembly 16 also having a hexagonal configuration, such as, for example, an outer surface of sheath 236 such that rotation of head locker 296 also rotates sheath 236 to further thread until the head is locked.

In some embodiments, inserting head locker 296 into pathway 270 of driver 1012 while assembly 16 of driver 1012 is coupled to bone screw 1208 prevents movement of receiver 234 of bone screw 1208 relative to shaft 206 of bone screw 1208 and/or inserting head locker 296 into pathway 270 of driver 12 while assembly 16 of driver 12 is coupled to bone screw 208 prevents movement of receiver 234 of bone screw 208 relative to shaft 206 of bone screw 208. In some embodiments, inserting head locker 296 into pathway 270 of driver 1012 while assembly 16 of driver 1012 is coupled to bone screw 1208 prevents movement of receiver 234 of bone screw 1208 relative to shaft 206 of bone screw 1208 by pressing a crown of bone screw 1208 against shaft 206 of bone screw 1208 in a manner that prevents movement of receiver 234 of bone screw 1208 relative to shaft 206 of bone screw 1208 and/or inserting head locker 296 into pathway 270 of driver 12 while assembly 16 of driver 12 is coupled to bone screw 208 prevents movement of receiver 234 of bone screw 208 relative to shaft 206 of bone screw 208 by pressing a crown of bone screw 208 against shaft 206 of bone screw 208 in a manner that prevents movement of receiver 234 of bone screw 208 relative to shaft 206 of bone screw 208.

Figure 40:
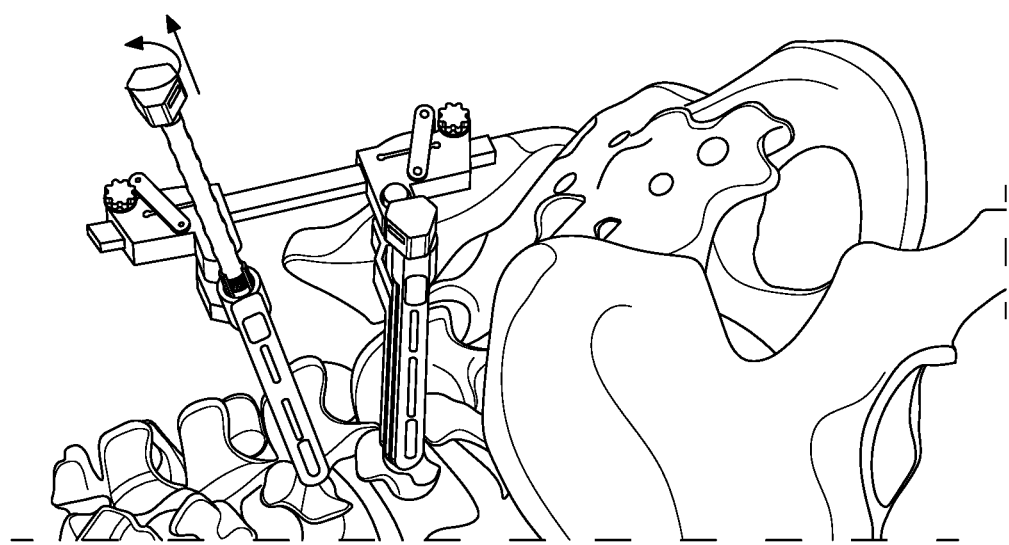
FIG. 40 is plan view of a component of the surgical instrument shown in FIG. 1 coupled to a component of the additional surgical instrument and a component of the second one of the surgical instruments shown in FIG. 1 coupled to the portion of the additional surgical instrument.

Once movement of receiver 234 of bone screw 1208 relative to shaft 206 of bone screw 1208 and/or movement of receiver 234 of bone screw 208 relative to shaft 206 of bone screw 208 is prevented by inserting head lockers 296 into assembly 16 of driver 1012 and/or assembly 16 of driver 12, head locker 296 and assembly 16 of driver 1012 can be removed from tower 288, as shown in FIG. 40. Likewise, head locker 296 and assembly 16 of driver 12 can be removed from tower 292, leaving only instrument 290 coupled to bone screws 208, 1208. A spinal rod can then be inserted between arms 230, 232 of bone screw 208 and between arms 230, 232 of bone screw 1208 to selectively position vertebra V2 relative to vertebra V1.

In some embodiments, assembly 16 can be used to axially align the retraction tower as its placed onto the screw in situ (and in the new configuration it also aligns to the rod slot plane so the tower is keyed properly to attach to the rocker holes). In addition to the retraction tower, assembly 16 can also be used to axially guide a "head locking tool" that pushes the crown of the screw down to temporarily lock the multiaxiality of the head. In some embodiments, this is needed to achieve parallel distraction rather than just rotating the head about the shank when trying to distract. In some embodiments, the head locker and assembly 16 are assembled in situ for combined removal and disassembly after the surgery. This reduces a step of removing independently.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
an outer assembly comprising an outer sleeve, an inner sleeve positioned in the outer sleeve, a shaft extending through the sleeves, a latch coupled to the inner sleeve, a knob coupled to the inner sleeve and a lever having a proximal end coupled to the knob and an opposite distal end coupled to the latch, a distal end of the shaft comprising a drive; and
an inner assembly comprising an outer sheath and an inner sheath extending through the outer sheath, the inner sheath having a proximal end positioned between the inner sleeve and the shaft and an opposite distal end comprising a threaded outer surface, the proximal end of the inner sheath including a groove,
wherein the knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve.

2. The surgical instrument recited in claim 1, wherein the knob translates relative to the inner sleeve to move the instrument between the first and second orientations.

3. The surgical instrument recited in claim 1, wherein the knob translates proximally relative to the inner sleeve to move the instrument from the first orientation to the second orientation.

4. The surgical instrument recited in claim 1, wherein the knob translates distally relative to the inner sleeve to move the instrument from the second orientation to the first orientation.

5. The surgical instrument recited in claim 1, wherein:
the knob is coupled to the inner sleeve by a pin that extends through the knob and into a slot of the sleeve; and
the pin translates relative to the inner sleeve within the slot as the instrument moves between the first and second orientations.

6. The surgical instrument recited in claim 1, wherein:
the knob is coupled to the inner sleeve by a pin that extends through the knob and the lever and into a slot of the sleeve; and
the pin translates proximally relative to the inner sleeve within the slot as the instrument moves from the first orientation to the second orientation.

7. The surgical instrument recited in claim 1, wherein the latch includes a proximal end and an opposite distal end that includes a tab, the tab being positioned in the groove when the instrument is in the first orientation and being spaced apart from the groove when the instrument is in the second orientation, the proximal end of the latch including a leaf spring.

8. The surgical instrument recited in claim 7, wherein the leaf spring engages the lever when the instrument is in the first orientation and is spaced apart from the lever when the instrument is in the second orientation.

9. The surgical instrument recited in claim 1, wherein the latch pivots relative to the inner sleeve as the instrument moves between the first and second orientations.

10. The surgical instrument recited in claim 1, wherein the latch is coupled to the inner sleeve by a pin that extends through the latch and into the inner sleeve, the latch pivoting relative to the inner sleeve about the pin as the instrument moves between the first and second orientations.

11. The surgical instrument recited in claim 1, wherein the instrument is biased to the first orientation.

12. The surgical instrument recited in claim 1, wherein the instrument is biased to the first orientation by a spring positioned between a proximal wall of the inner sleeve and a distal wall of the knob.

13. The surgical instrument recited in claim 1, wherein the inner sleeve has an inner surface defining a hexagonal configuration and the inner sheath comprises an outer surface having a hexagonal configuration that mates with the inner surface of the inner sleeve that defines the hexagonal configuration of the inner sleeve such that rotating the inner sleeve relative to the outer sleeve also rotates the inner sheath relative to the outer sleeve.

14. The surgical instrument recited in claim 1, wherein shaft is permanently fixed relative to the outer sleeve.

15. The surgical instrument recited in claim 1, wherein the inner assembly is removable from the outer assembly when the instrument is in the second orientation.

16. The surgical instrument recited in claim 1, wherein the drive is configured for engagement with a shank of a bone screw and the outer sheath comprises spaced apart tabs each configured for disposal between arms of a head of the bone screw, the outer sheath being rotatable relative to the inner sheath.

17. The surgical instrument recited in claim 16, wherein the inner sheath includes a circumferential recess and the outer sheath includes opposing apertures, the instrument including pins each extending through one of the apertures and into the recess.

18. The surgical instrument recited in claim 17, wherein the apertures each extend through one of the tabs.

19. A surgical instrument comprising:
an outer assembly comprising an outer sleeve defining a longitudinal axis, an inner sleeve rotatably positioned in the outer sleeve, a shaft extending through the sleeves, a latch coupled to the inner sleeve, a knob coupled to the inner sleeve and a lever having a proximal end coupled to the knob and an opposite distal end fixed to the latch, a distal end of the shaft comprising a drive configured for engagement with a socket of a shank of a bone screw, the shaft being permanently fixed relative to the outer sleeve; and an inner assembly comprising an outer sheath and an inner sheath rotatably positioned in the outer sheath, the inner sheath having a proximal end positioned between the inner sleeve and the shaft and an opposite distal end comprising a threaded outer surface configured for engagement with a threaded inner surface of a head of the bone screw, the outer sheath comprising spaced apart tabs each configured for disposal between arms of the head, the proximal end of the inner sheath including a circumferential groove, wherein the knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve, wherein the knob translates relative to the inner sleeve to move the instrument between the first and second orientations, wherein the latch pivots relative to the inner sleeve about a transverse axis that extends perpendicular to the longitudinal axis as the instrument moves between the first and second orientations, and wherein the inner sleeve has an inner surface defining a hexagonal configuration and the inner sheath comprises an outer surface having a hexagonal configuration that mates with the inner surface of the inner sleeve that defines the hexagonal configuration of the inner sleeve such that rotating the inner sleeve relative to the outer sleeve also rotates the inner sheath relative to the outer sleeve.

20. A surgical system comprising:

a bone screw comprising a shank and a head rotatably coupled to the shank, the shank defining a socket, the head including spaced apart arms defining an implant cavity therebetween, the arms each including a threaded inner surface; and a surgical instrument comprising:

an outer assembly comprising an outer sleeve, an inner sleeve positioned in the outer sleeve, a shaft extending through the sleeves, a latch coupled to the inner sleeve, a knob coupled to the inner sleeve and a lever having a proximal end coupled to the knob and an opposite distal end coupled to the latch, a distal end of the shaft comprising a drive configured for disposal in the socket, and an inner assembly comprising an outer sheath and an inner sheath extending through the outer sheath, the inner sheath having a proximal end positioned between the inner sleeve and the shaft and an opposite distal end comprising a threaded outer surface configured for engagement with the threaded inner surfaces of the arms, the outer sheath comprising spaced apart tabs each configured for disposal between the arms when the drive is positioned in the socket and the threaded outer surface engages the threaded inner surfaces, the proximal end of the inner sheath including a groove, wherein the knob is movable relative to the inner sleeve to move the instrument between a first orientation in which the latch is positioned in the groove and the inner sheath is prevented from translating relative to the inner sleeve and a second orientation in which the latch is spaced apart from the groove and the inner sheath is translatable relative to the inner sleeve.

\* \* \* \* \*